(12) United States Patent
Goldenberg et al.

(10) Patent No.: US 8,275,443 B2
(45) Date of Patent: Sep. 25, 2012

(54) MRI COMPATIBLE ROBOT WITH CALIBRATION PHANTOM AND PHANTOM

(75) Inventors: Andrew A. Goldenberg, Toronto (CA); Yi Yang, Toronto (CA); Liang Ma, Toronto (CA); John Trachenberg, Toronto (CA); Walter Kucharczyk, Toronto (CA); Masoom Haider, Richmond Hill (CA); Marshall Stephen Sussman, Toronto (CA); Uri Lindner, Toronto (CA); Robert Anthonie Weersink, Toronto (CA)

(73) Assignees: Engineering Services Inc., Toronto, On (CA); University Health Network, Toronto, On (CA)

( * ) Notice: Subject to any disclaimer, the term of this patent is extended or adjusted under 35 U.S.C. 154(b) by 525 days.

(21) Appl. No.: 12/457,707

(22) Filed: Jun. 18, 2009

(65) Prior Publication Data
US 2009/0326364 A1 Dec. 31, 2009

Related U.S. Application Data

(60) Provisional application No. 61/129,319, filed on Jun. 18, 2008.

(51) Int. Cl.
*A61B 5/055* (2006.01)
(52) U.S. Cl. .................. 600/411; 600/410
(58) Field of Classification Search .......... 600/410, 600/411; 324/307
See application file for complete search history.

(56) References Cited

U.S. PATENT DOCUMENTS

| | | | |
|---|---|---|---|
| 4,501,414 A | 2/1985 | Mason et al. | |
| 4,888,555 A | 12/1989 | Vaughan et al. | |
| 4,922,915 A | 5/1990 | Arnold et al. | |
| 4,923,459 A | 5/1990 | Nambu | |
| 5,071,602 A | 12/1991 | Nambu et al. | |
| 5,312,755 A | 5/1994 | Madsen et al. | |
| 6,318,146 B1 | 11/2001 | Madsen et al. | |
| 6,675,035 B1 | 1/2004 | Grable et al. | |
| D569,977 S | 5/2008 | Luginbuhl et al. | |

(Continued)

FOREIGN PATENT DOCUMENTS
EP 0919203 6/1999
(Continued)

OTHER PUBLICATIONS

Camacho et al, Nonsusceptibility Artifacts Due to Metallic Objects in MR Imaging, JMRI, vol. 5, No. 1, Jan./Feb. 1995, pp. 75-88.

(Continued)

*Primary Examiner* — Michael Rozanski
(74) *Attorney, Agent, or Firm* — Hill & Schumacher

(57) ABSTRACT

A medical robot for use inside an MRI includes a horizontal motion assembly, a vertical motion assembly and a controller. The horizontal motion assembly and the vertical assembly each includes a motion joint, an ultrasonic motor operably connected to the motion joint and an encoder operably connected to the ultrasonic motor. The motor and encoder are positioned proximate to the joint of the respective horizontal motion assembly and vertical motion assembly. Each motor has a cross section positioned in one of the axial and sagittal plane of the MRI. A medical instrument assembly is operably connectable to one of the moving joint of the vertical motion assembly. The controller is operably connected to the horizontal motion joint and the vertical motion joint and it is adapted to be powered off when the magnetic resonance imager is being used to collect images.

35 Claims, 29 Drawing Sheets

U.S. PATENT DOCUMENTS

| | | | |
|---|---|---|---|
| 2001/0041838 A1 | 11/2001 | Holupka et al. | |
| 2003/0055436 A1 | 3/2003 | Daum et al. | |
| 2003/0065310 A1 | 4/2003 | Wang et al. | |
| 2003/0181807 A1 | 9/2003 | Murphy et al. | |
| 2005/0211905 A1 | 9/2005 | Stark | |
| 2007/0039101 A1 | 2/2007 | Luginbuhl et al. | |
| 2007/0088340 A1 | 4/2007 | Brock et al. | |
| 2007/0089557 A1 | 4/2007 | Solomon et al. | |
| 2007/0230757 A1 | 10/2007 | Trachtenberg et al. | |
| 2007/0262774 A1 | 11/2007 | Schilling | |
| 2008/0004481 A1 | 1/2008 | Bax et al. | |
| 2008/0255461 A1 | 10/2008 | Weersink et al. | |
| 2009/0326365 A1* | 12/2009 | Goldenberg et al. | 600/411 |
| 2010/0125192 A1* | 5/2010 | Chopra et al. | 600/411 |

FOREIGN PATENT DOCUMENTS

| | | |
|---|---|---|
| EP | 0922438 | 6/1999 |
| EP | 1103229 | 5/2001 |
| EP | 1815950 | 8/2007 |
| EP | 1839599 | 10/2007 |
| FR | 2576510 | 8/1986 |
| JP | 9266892 | 10/1997 |
| JP | 10057336 | 3/1998 |
| WO | 95/16396 | 6/1995 |
| WO | 99/37220 | 7/1999 |
| WO | 00/49960 | 8/2000 |
| WO | 2004/019799 | 3/2004 |
| WO | 2004/029881 | 4/2004 |
| WO | 2004/080529 | 9/2004 |
| WO | 2005/046753 | 5/2005 |
| WO | 2005/092197 | 10/2005 |
| WO | 2006/089426 | 8/2006 |
| WO | 2007/065013 | 6/2007 |
| WO | 2007/106558 | 9/2007 |
| WO | 2007/106877 | 9/2007 |
| WO | 2008/031077 | 3/2008 |
| WO | 2008042423 | 4/2008 |
| WO | 2008/059263 | 5/2008 |

OTHER PUBLICATIONS

Chopra et al, MRI—compatible transurethral ultrasound system for the treatment of localized prostate cancer using rotational control, Med Phys. 35(4)Apr. 2008, pp. 1346-1357.

* cited by examiner

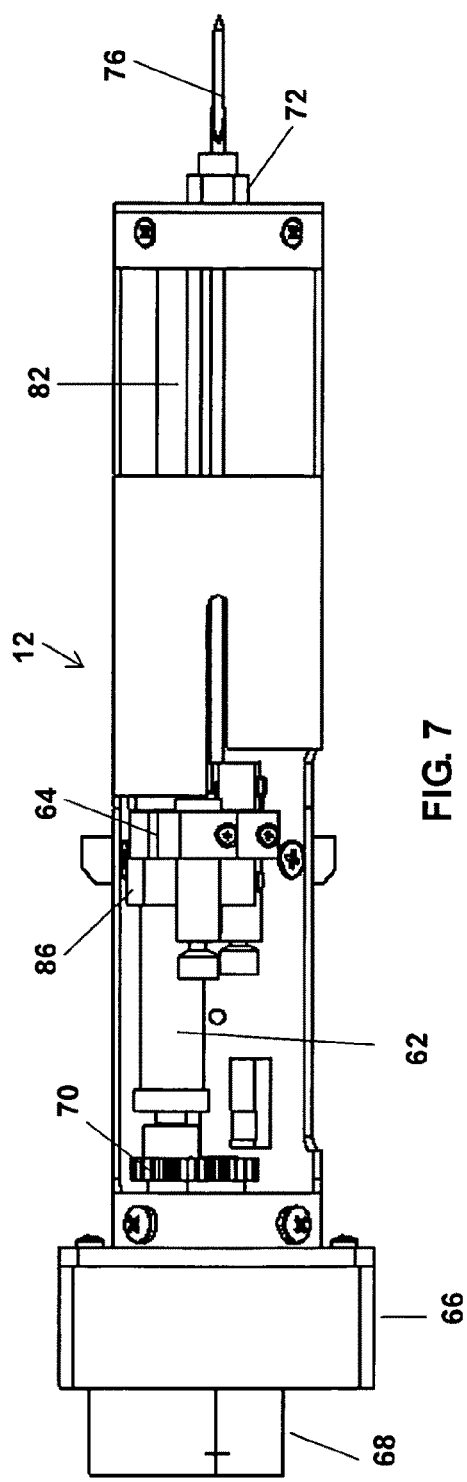
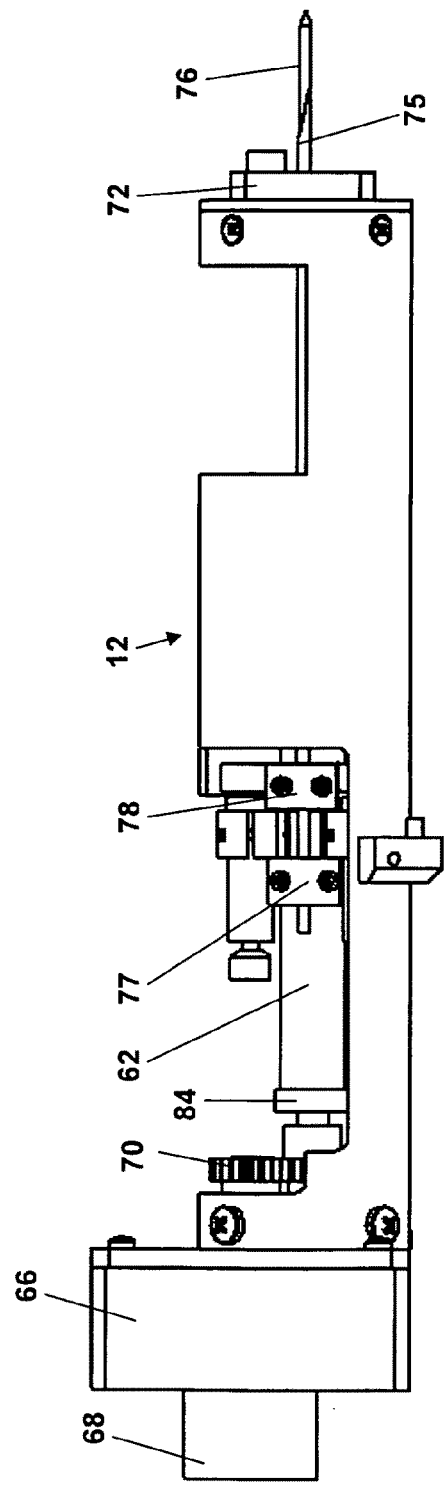
FIG. 7
FIG. 8

(a)　　　　　(b)　　　　　(c)

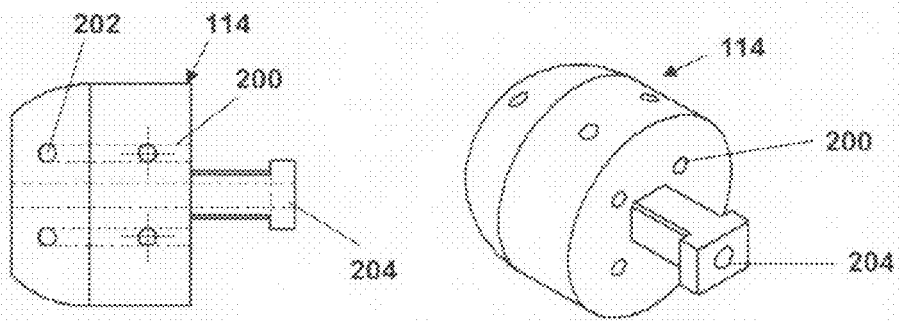
FIG. 35   FIG. 34
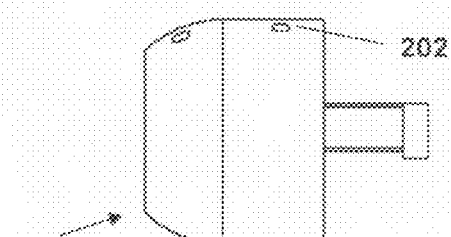   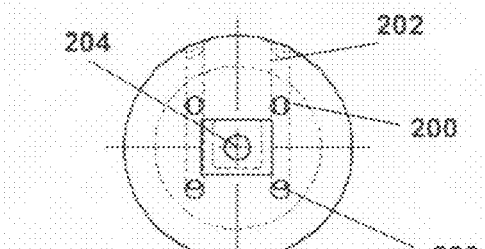
FIG. 36   FIG. 37
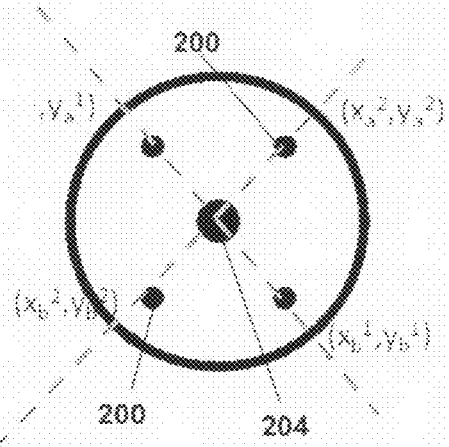
FIG. 38

MRI COMPATIBLE ROBOT WITH CALIBRATION PHANTOM AND PHANTOM

CROSS REFERENCE TO RELATED PATENT APPLICATION

This patent application relates to U.S. Provisional Patent Application Ser. No. 61/129,319 filed on Jun. 18, 2008 entitled MEDICAL ROBOT FOR USE IN A MRI which is incorporated herein by reference in its entirety.

FIELD OF THE INVENTION

This invention relates to medical robots and in particular medical robots for use in a magnetic resonance imaging device.

BACKGROUND OF THE INVENTION

Medical resonance imaging (MRI) devices are well known medical tools and are used extensively for diagnostic purposes. More recently it has become evident that it would be advantageous to provide a device that could be used within a close-bore MRI to perform surgery by remote control. Some medical robots have been developed however each has some significant limitations. Specifically there have been suggested some medical robots that use motors that are positioned 1 to 2 meters from the isocentre of the MRI (in fact outside the bore) and are actuated through mechanical linkages. Others have suggested remote manual actuation; zone control of MR-compatibility: no magnetic and electric components at less than 100 cm from the isocenter; motor driver and controller at 7 m away with shielded cables; motor electronics and power supply shielded in Farady cage; power to motor driver cut-off during scanning; and use of all-pneumatics that leads to larger robots. None of these robots provides a solution using ultrasonic motors that are positionable inside the bore near the isocentre of the MRI.

It will be appreciated by those skilled in the art that there is a need for reliable robots that can be used in an MRI. Further it would be advantageous to provide a medical robot with a method of calibration that is easy to use. Further it would be advantageous to provide a phantom that can mimic certain anatomical features that can be used for calibrating the robot, training surgeons and other tasks associated with the use of a robot in an MRI. It would be advantageous to provide a device that wherein a portion of it may be visible on an MR image. It would also be advantageous to provide a method of determining the best trajectory for a needle. In addition it would be useful to provide a platform for use in an MRI that includes a patient receiving portion and a medical robot is adapted to be attached thereto.

SUMMARY OF THE INVENTION

In one aspect of the invention there is a medical robot for use inside a magnetic resonance imager having an axial plane defined by a vertical axis and a sagittal plane defined by the lateral axis. The medical robot is connectable to a medical instrument assembly. The medical robot includes a horizontal motion assembly, a vertical motion assembly and a controller. The horizontal motion assembly includes a motion joint, an ultrasonic motor operably connected to the motion joint and an encoder operably connected to the ultrasonic motor. The ultrasonic motor and the encoder are positioned proximate to the joint. The motor has a cross section positioned in one of the axial and sagittal plane. The vertical motion assembly is operably connected to the horizontal motion assembly. The vertical motion assembly includes a motion joint, an ultrasonic motor operably connected to the motion joint and an encoder operably connected to the ultrasonic motor. The ultrasonic motor and the encoder are positioned proximate to the joint. The medical instrument assembly is operably connectable to one of the moving joint of the vertical motion assembly and the motion joint of the horizontal motion assembly. The motor has a cross section positioned in one of the axial and sagittal plane. The controller is operably connected to the horizontal motion joint and the vertical motion joint. The controller is adapted to be powered off when the magnetic resonance imager is being used to collect images.

In another aspect of the invention there is a phantom for use in association with a magnetic resonance imager. The phantom includes a phantom organ at risk made of a first predetermined material; a phantom treatable portion made of a second predetermined material different from the first predetermined material and differentiable from the first predetermined material in a magnetic resonance image; and a phantom surrounding structure of a third predetermined material and the third predetermined material is different from the first and second predetermined material and differentiable from the first and second predetermined material in a magnetic resonance image.

In a further aspect of the invention there is a calibration phantom for use in association with a medical instrument. The calibration phantom includes a housing that is attachable to a predetermined location on the medical instrument; and at least one channel capable of being visible in a magnetic resonance image, the channel being at a predetermined location to a point of interest in the medical instrument.

In a further aspect of the invention a platform for use in association with a medical robot includes a platform having a robot guide adapted to receive the medical robot; and a patient receiving portion adapted to adjustably position a patient thereon.

In another aspect of the invention there is provided a medical instrument comprising a laser fiber having a surrounding channel filled with a mixture of water and magnetic resonance imager visible fluid.

In another aspect of the invention there is provided a method to determine the needle trajectory comprising the steps of: providing images of a predetermined area; determining the location of an irregular zone on the images; calculating a planned target volume from the location of the irregular zone; calculating the treatment zone whereby the treatment zone covers the planned target volume; determining the starting needle position within a predetermined range; and calculating the needle trajectory from the starting needle position to the planned target zone.

Further features of the invention will be described or will become apparent in the course of the following detailed description.

BRIEF DESCRIPTION OF THE DRAWINGS

The invention will now be described by way of example only, with reference to the accompanying drawings, in which:

FIG. 7 is a top view of the medical instrument assembly of FIG. 6;

FIG. 8 is a side view of the medical instrument assembly of FIGS. 6 and 7;

FIG. 34 is a perspective view of an embodiment of the calibration phantom of FIG. 33;

FIG. 35 is a top view of the calibration phantom of FIG. 34;

FIG. 36 is a side view of the calibration phantom of FIG. 34;

FIG. 37 is a back view of the calibration phantom of FIG. 34;

FIG. 38 is a schematic diagram similar to that shown in FIG. 33 a) but showing the imaginary lines in the calculations;

DETAILED DESCRIPTION OF THE INVENTION

The present invention relates to performing medical procedures remotely using a robot under the guidance of magnetic resonance imaging (MRI). One function of the robot is to deliver one or more medical device to a location within the body as selected based on magnetic resonance (MR) images of the body. The MR images are also used to monitor the intervention and the therapy provided in real-time. The robotic device is MRI compatible whilst inside the MRI scanner.

In one application, the robotic device is used for tissue ablation. In this application, the objective is to destroy a particular region of tissue that may contain a certain size and type of cancerous tumor through either heating or cooling. In the present context, the robot will deliver a heating or cooling device to the MRI-specified location. Heating or cooling will then destroy the tissue in the targeted region. In this application, the temperature change in tissue is monitored as the heating/cooling is being delivered. The temperature change is monitored to determine that a sufficient temperature change is achieved to destroy the targeted tissue, as well as to ensure that excess temperature change (and therefore damage) does not occur in non-targeted (i.e. healthy) tissue. A method of monitoring the temperature change is outlined in more detail below.

Figure 1:
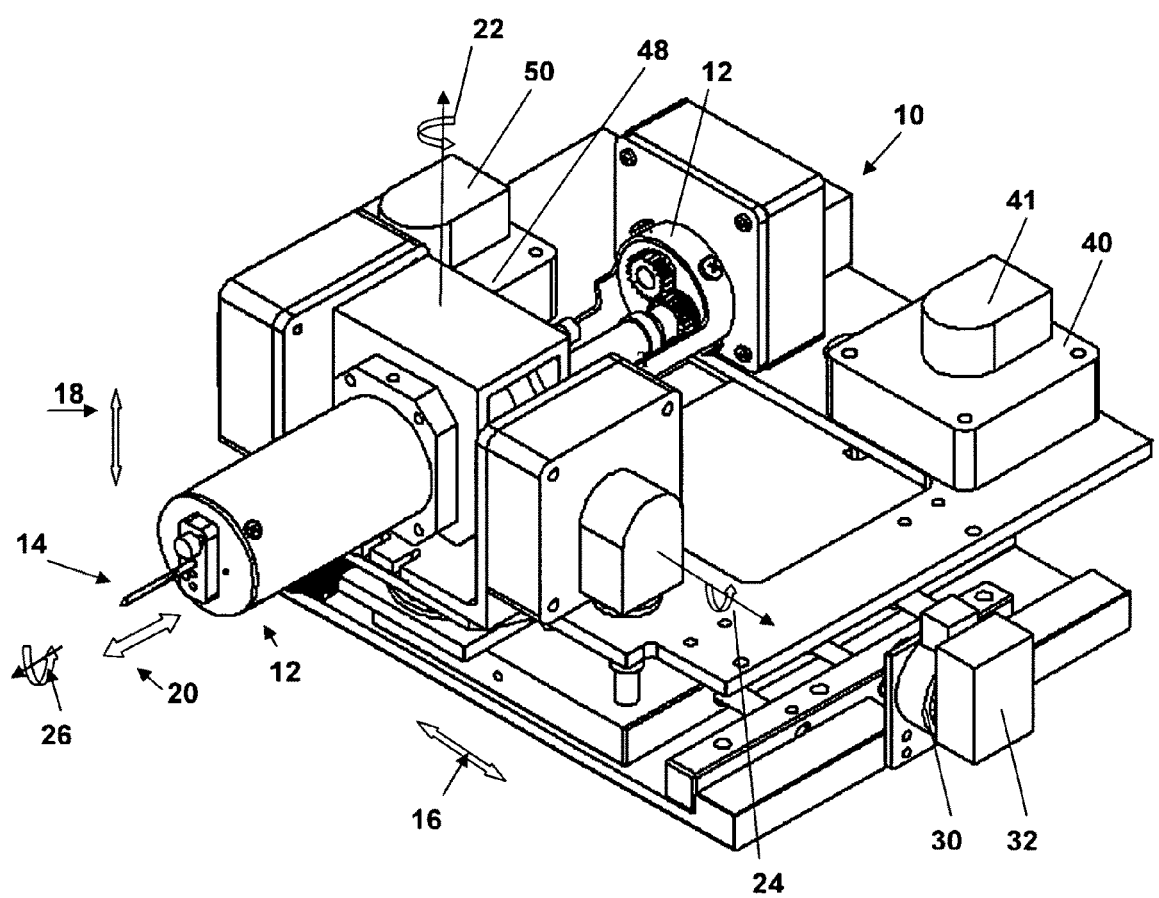
FIG. 1 is a perspective view of the medical robot of the present invention having a medical instrument assembly positioned thereon.

Referring to FIG. 1, the medical robot of the present invention is shown generally at 10. The medical robot 10 has a medical instrument assembly or trocar 12 attached thereto. The combined medical robot 10 and medical instrument assembly 12 is a six degree of freedom robot which is used to automatically locate (orientation and position) the tip of the trocar needle 14 at a selected location near the patient before manually controlled penetration. By way of example, when medical robot 10 is used for prostate surgery the tip of the trocar needle 14 is located near the perineum before manually controlled penetration. It will be appreciated that penetration may also be automatic. The combined medical robot 10 and medical instrument 12 has three linear motion joints and three rotational joints, described in more detail below. As shown by the arrows in FIG. 1, the three linear joints effect horizontal translation 16, vertical translation 18 and needle penetration or insertion 20 and the three rotational joints effect pan 22, tilt 24 and roll 26.

Figure 2:
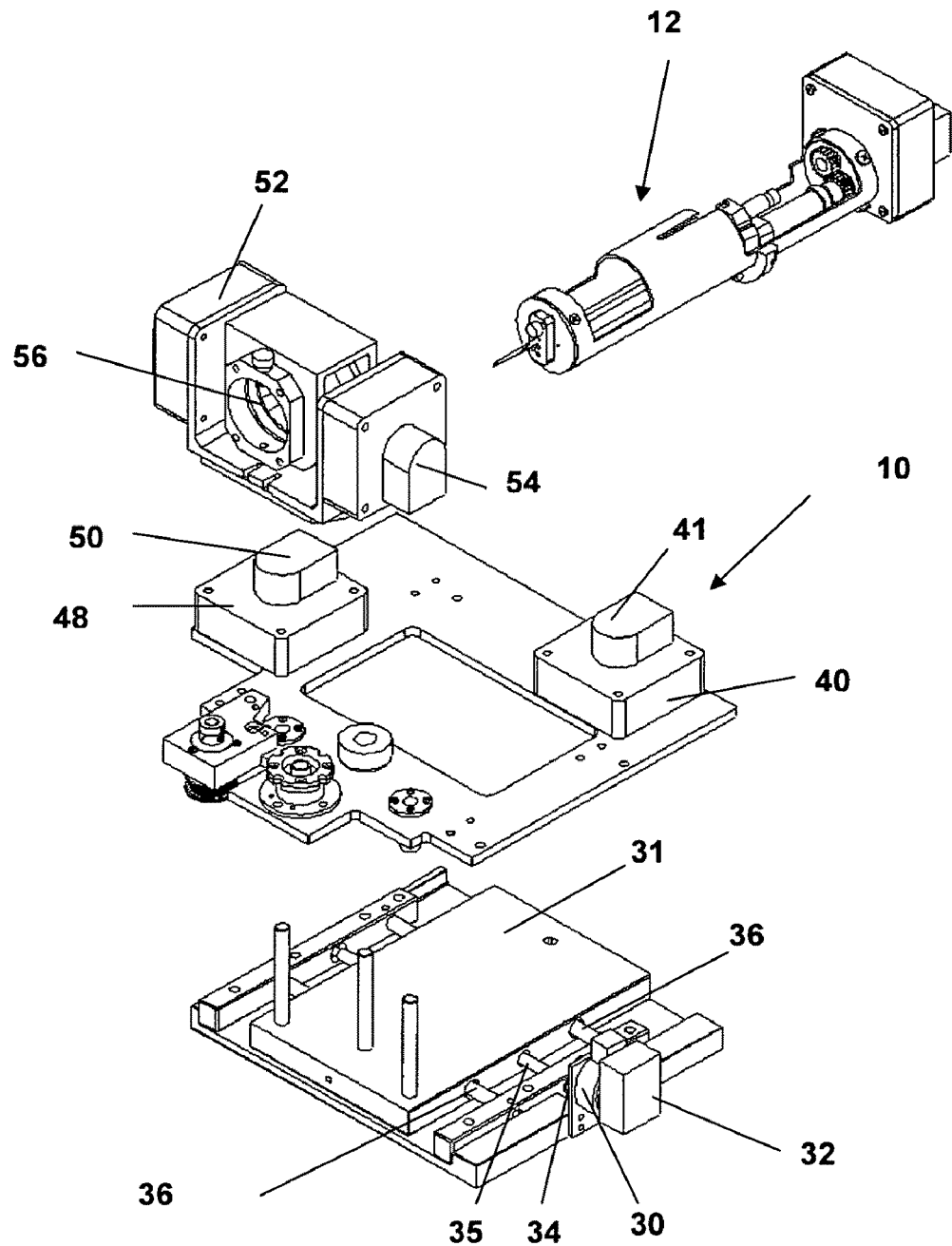
FIG. 2 is a blown apart perspective view of the medical robot and medical instrument assembly of FIG. 1.
Figure 3:
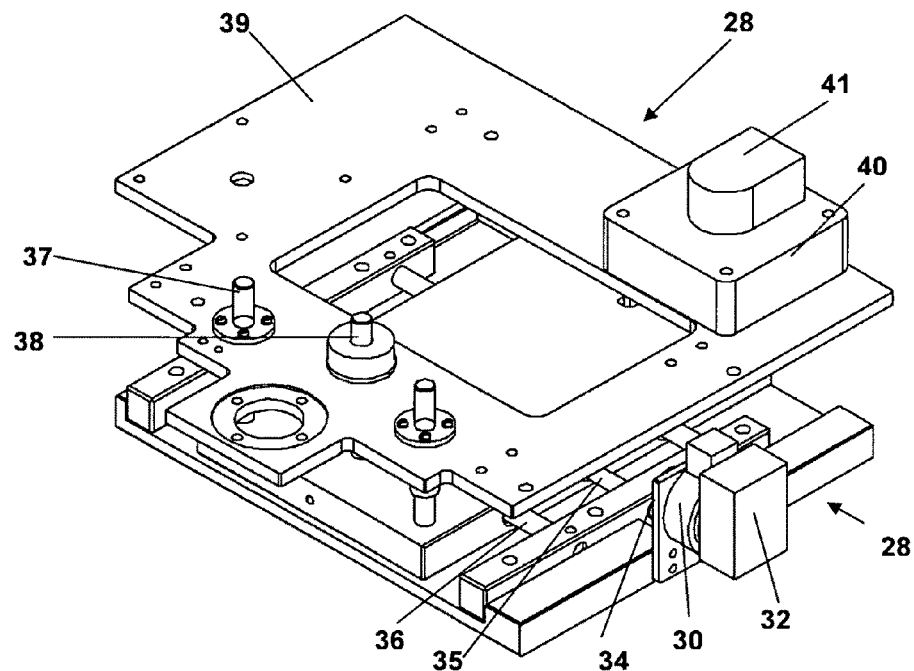
FIG. 3 is a perspective view of the horizontal and vertical linear motion portions of the medical robot.

Medical robot 10 has two separate linear motion joints to implement horizontal 16 and vertical translations 18, respectively. FIG. 3 shows the structure of the robot base 28 that includes joints to translate the motion horizontally and vertically. The horizontal motion joint consists of a horizontal ultrasonic motor 30 (preferably USR30-E3N) with a horizontal encoder 32 a pair of spur gears 34, a horizontal acme lead screw and nut 36, a pair of horizontal linear guides 36 and a horizontal moving plate (shown in FIG. 2) 31. The lead screw 35 unit is equipped with ceramic ball bearings. The actuators are ultrasonic motors that being retentive can lock the joint into position so that no motor brakes are needed. As can been seen the figures horizontal ultrasonic motor 30 and horizontal encoder 32 are positioned proximate to the horizontal motion assembly including the spur gears 34, the horizontal acme lead screw and nut 35 and the horizontal linear guides 36.

The vertical motion joint consists of a vertical ultrasonic motor 40 (preferably USR60-E3N) with a vertical encoder 41, a timing belt and a pair of pulleys (not shown), a pair of vertical linear guides 37, a vertical acme lead screw and nut 38, and a vertical moving plate 39. As can be seen in the figures the vertical ultrasonic motor 40 and vertical encoder 41 are positioned proximate to vertical motion assembly including the timing belt, pulleys, vertical linear guides 37, and vertical acme lead screw and nut 38. All the parts in base 28 including the horizontal motion joint and the vertical motion joint are made either of Aluminum or plastic. They both have suitable magnetic susceptibility.

Figure 4:
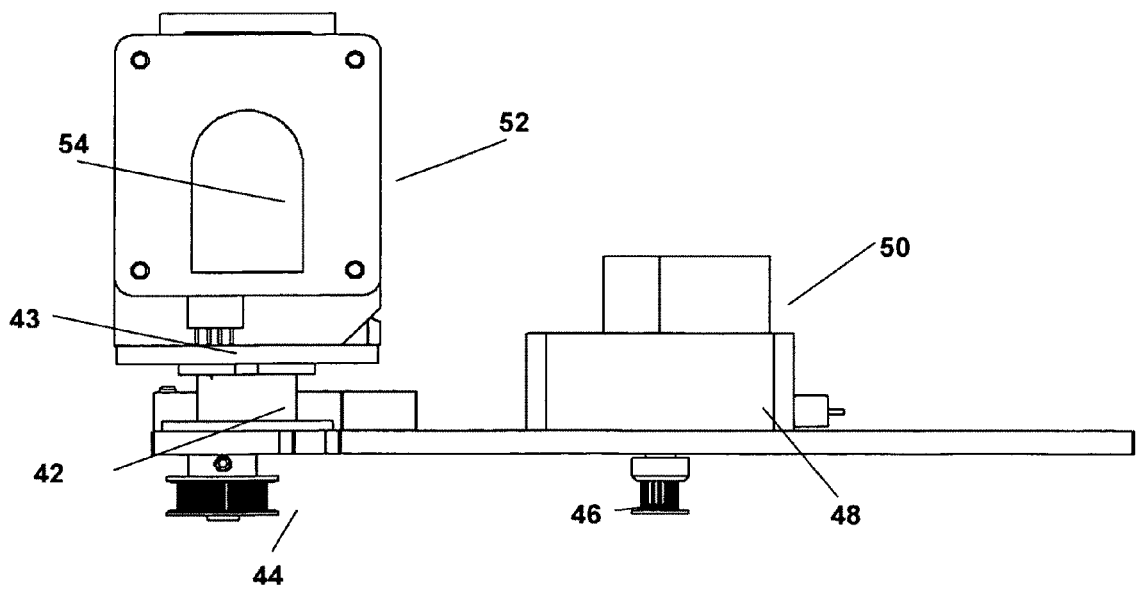
FIG. 4 is a side view of the pan tilt and rotational portions of the medical robot.
Figure 5:
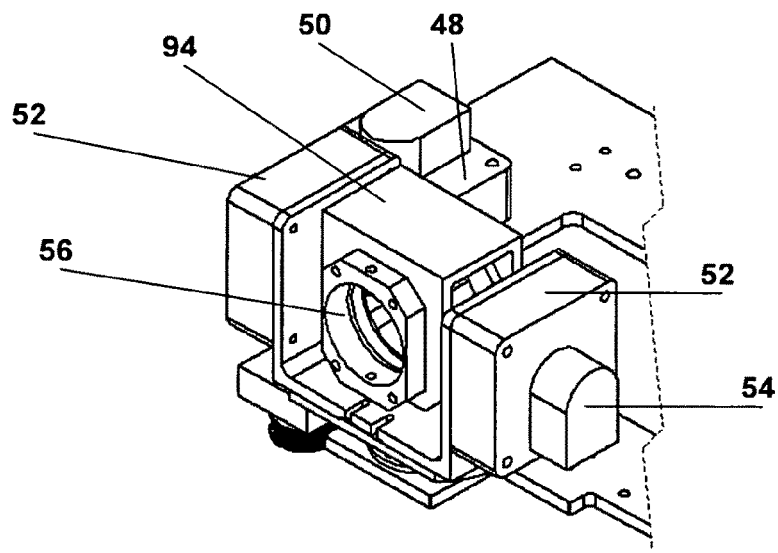
FIG. 5 is a perspective view of the pan tilt and rotational portions of the medical robot.

The medical robot 10 has three rotation joints: pan (rotation in horizontal plane), tilt (elevation in vertical plane) and roll (rotation), as best seen in FIGS. 4 and 5. The pan joint unit consists of a pan shaft assembly 42, a pair of spur gears 43, a timing belt 44 and pulleys 46, and a pan ultrasonic motor 48 (preferably USR60-E3N) with a pan encoder 50. The pan ultrasonic motor 48 and pan encoder 50 are positioned proximate to the pan assembly including the pan shaft assembly 42, a pair of spur gears, the timing belt 44 and pulleys 46. The tilt and roll joints are composed of two tilt and roll ultrasonic motors 52 (preferably USR60-E3N) with tilt and roll encoders 54 and a bevel gears differential mechanism 56. The transmission is from motors 52 to smaller driving bevel gears and then to larger driven bevel gears. When the two driving bevel gears rotate at same speed and same direction, the tilting movement is realized; and when they rotate at same speed and reverse direction, the rolling movement is realized. Because the two motors work together, a larger torque output is obtained.

Figure 6:
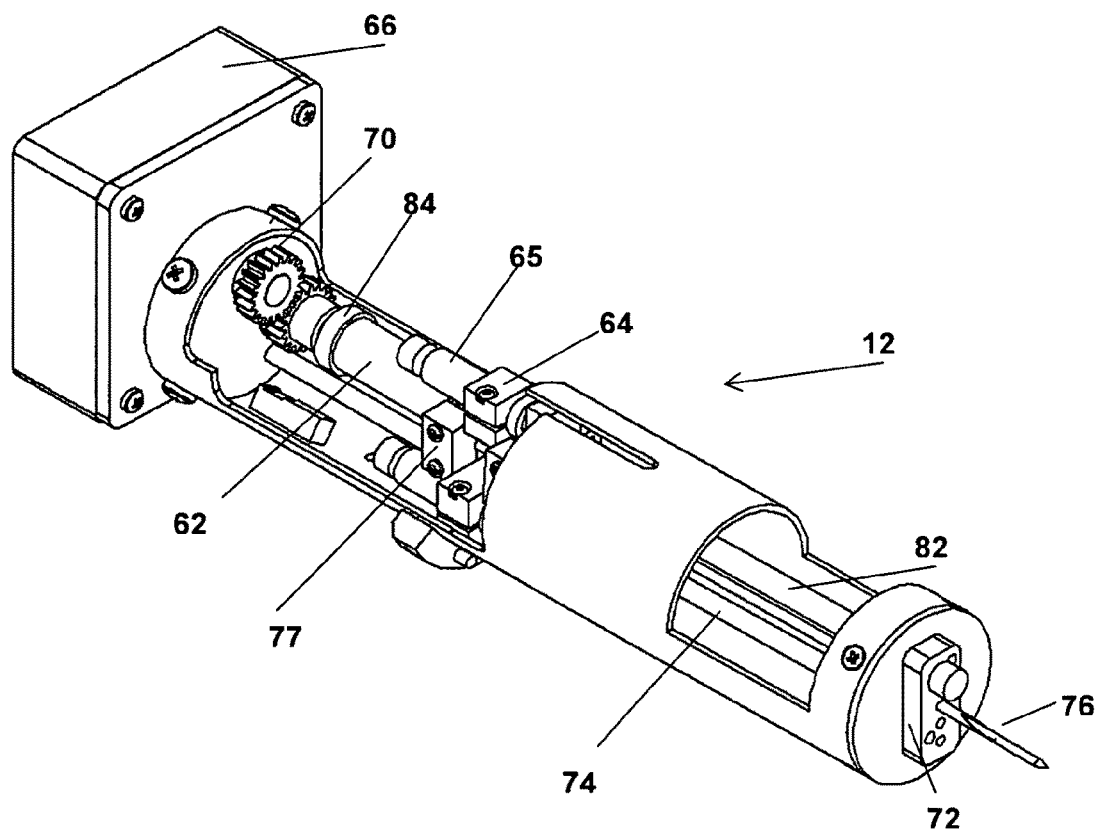
FIG. 6 is a perspective view of the medical instrument assembly or trocar that is attachable to the medical robot of the present invention.
Figure 11:
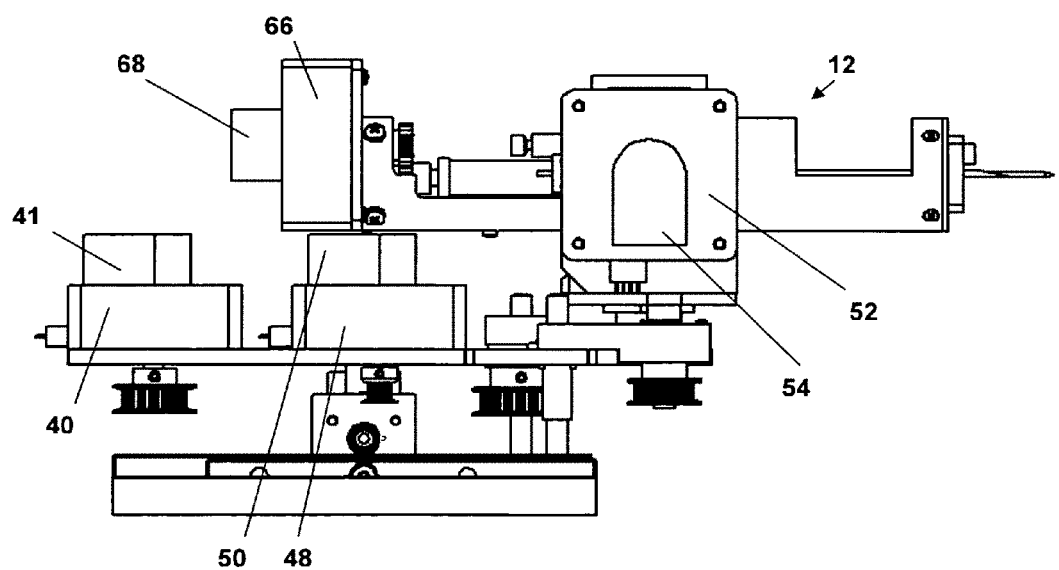
FIG. 11 is a side view of the medical robot with the medical instrument assembly attached thereto.

The medical instrument assembly 12 used with the medical robot 10 may have a variety functions. In the configuration shown herein the medical instrument assembly moves the end point so as to effect insertion or penetration. Referring to FIGS. 6, 7 and 8, the medical instrument assembly or trocar module 12 shown herein is for laser ablation. The main parts of the medical instrument assembly 12 include a "needle" (or "trocar") tool; pushing and pulling mechanism 62; tapping block 64, tapping cylinder 65, ultrasonic motor 66 (preferably USR60-E3N) with encoder 68 (as seen in FIG. 11), gears 70, guiding block 72 and guiding shaft 74. The pushing and pulling mechanism provide linear motion.

The medical instrument assembly 12 consists of a titanium sheath 75 and a water cooled power laser applicator 76 which protects or cools the laser diffuser. The pushing and pulling mechanism 62, comprises a lead screw 82, a pusher with nut 84, a holder 86 of the irrigated power laser applicator 76 and a sheathe locker 78. The pushing and pulling mechanism 62 is adapted to push the needle tools to the target and to retract the sheathe for exposing the laser diffuser tip. It is also adapted to pull the "needle" tool back after the surgical operation is done. Accordingly the pushing and pulling mechanism provides linear motion and is the sixth degree of freedom for the medical robot 10. The lead screw 82 is equipped with a pair of ceramic ball bearings. In order to get a high insertion velocity of the needle tool, a tapping block 64 that is pneumatically driven is added. It will be appreciated by those skilled in the art that the laser diffuser could be replaced with a laser diffuser with a retractable titanium sheath, a biopsy tool and a brachytherapy tool.

Figure 9:
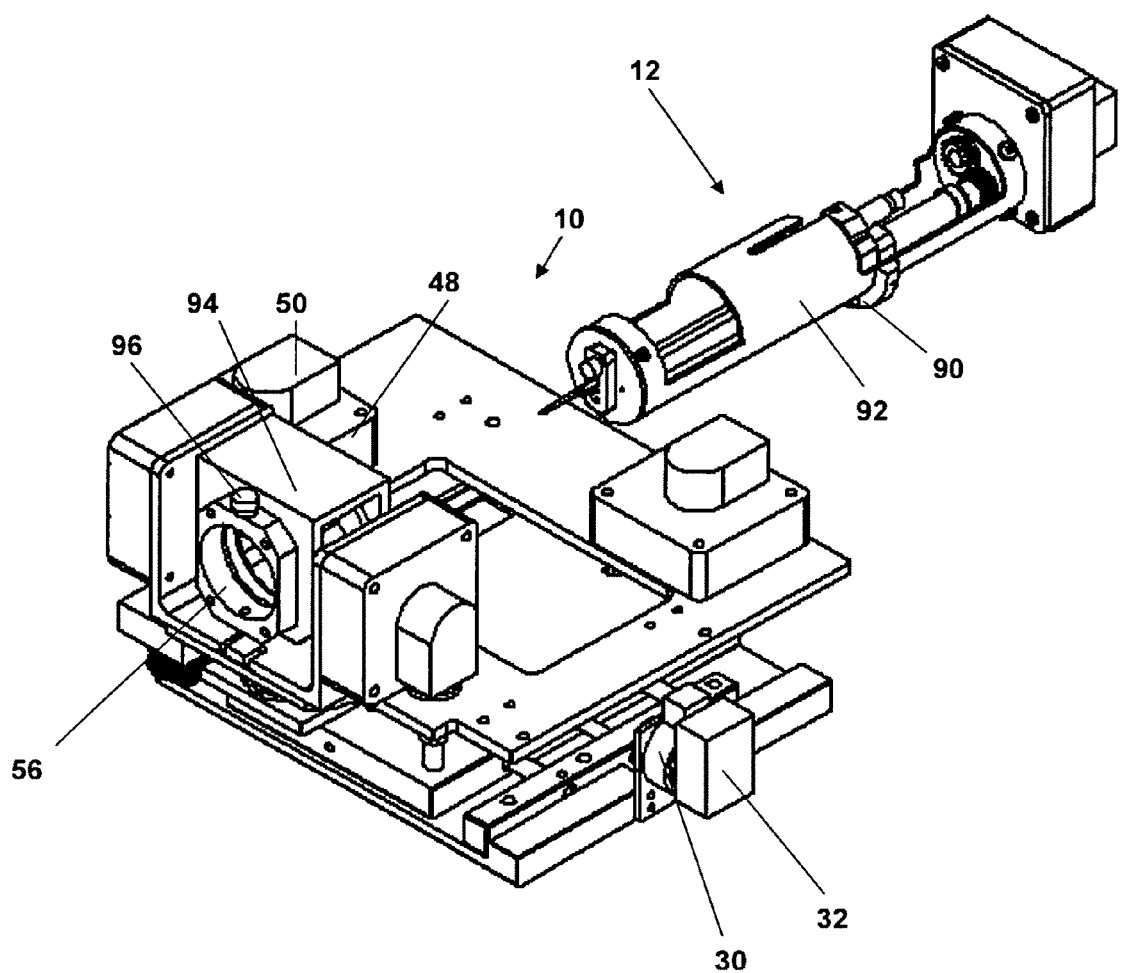
FIG. 9 is a perspective view of the medical robot of the present invention with the medical instrument assembly ready to be attached thereto.
Figure 10:
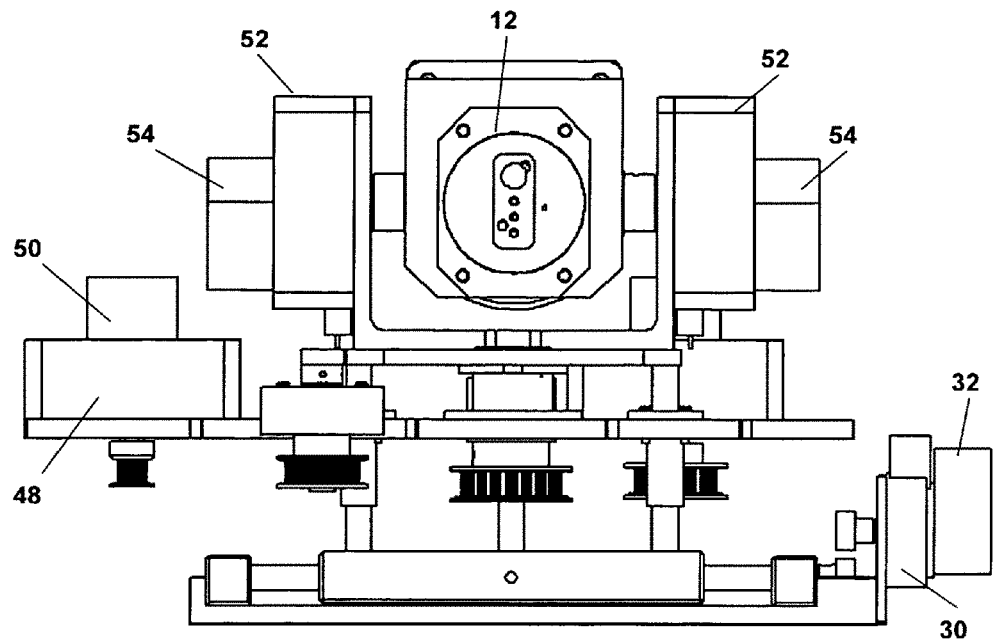
FIG. 10 is a front view of the medical robot with the medical instrument assembly attached thereto.

FIGS. 10 and 11 show the medical instrument assembly 12 attached to the medical robot 10 and FIG. 9 shows them just prior to attachment. The combined device has six degrees of freedom wherein five degrees of freedom are in the medical robot 10 and one degree of freedom is in the medical instrument assembly 12. In the embodiment shown herein the medical instrument assembly 12 is a trocar device for laser ablation. However, the medical instrument as could also be a device for use with obtaining biopsies or a device for brachytherapy. It will be appreciated by those skilled in the art that the medical instrument assembly could also be designed such that any or all of the pan tilt and roll functions were part of the medical instrument assembly rather than the medical robot.

In order to allow the operator easily and quickly to substitute the medical instrument assemblies 12 without having to make adjustments to the medical robot 10, simple interfaces between the medical robot 10 and the medical instrument assembly 12 are provided. A positioning block 90 with two pins is attached under the shell 92 of each medical instrument assembly 12. The shell 92 of the medical instrument assembly 12 is plugged into the hollow of the support block 94 that is coupled with a large hollow bevel gear 56 on the medical robot 10. The positioning block 90 is positioned against the rear side of the support block 94 and then locked in place with a thumb screw 96. Thus the medical instrument assembly 12 can be quickly mounted on the base unit or medical robot 10. Similarly it can be quickly and easily removed by unlocking with the thumb screw 96 and pulling the medical instrument assembly 12 out of the support block 94.

Figure 12:
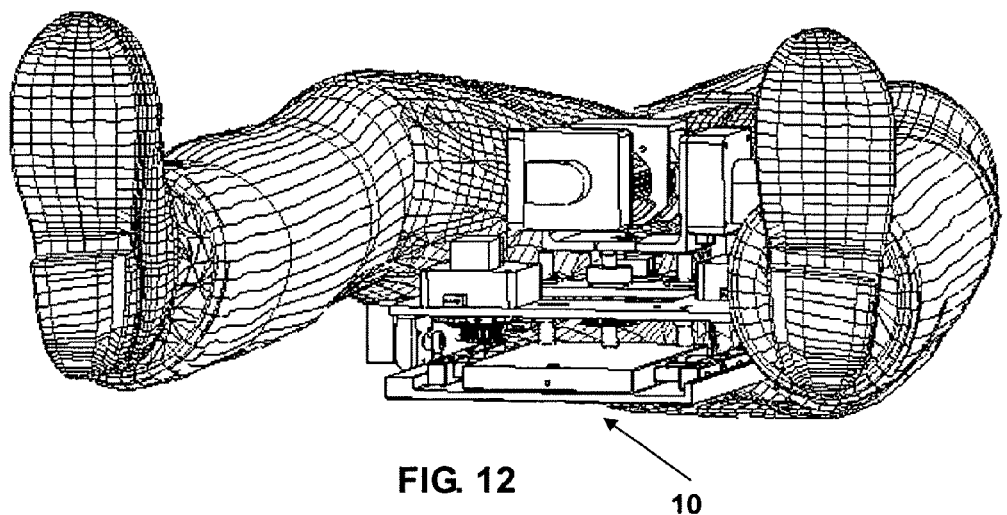
FIG. 12 is a perspective view of the medical robot with the medical instrument assembly attached thereto shown between a person's legs.
Figure 13:
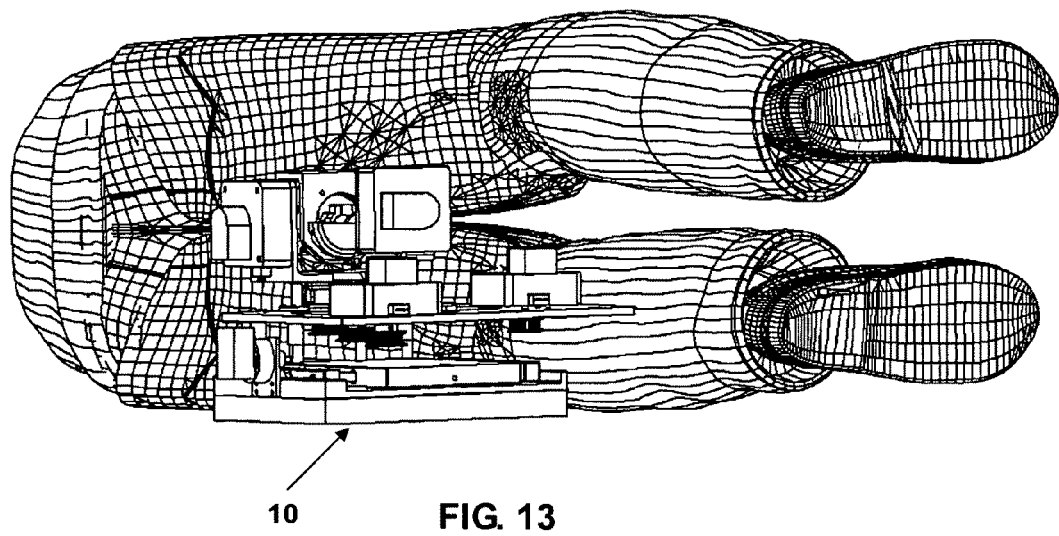
FIG. 13 is a perspective view of the medical robot with the medical instrument assembly attached thereto shown position proximate to a person who is positioned on their side.

The combined medical robot 10 and medical instrument assembly 12 can be positioned between a person's legs when the person is lying on their back as shown in FIG. 12 or positioned below a person's bottom when the person is positioned on their side as shown in FIG. 13.

An alternate embodiment of the medical robot with an alternate embodiment of a trocar is shown in FIGS. 14 to 24.

Figure 14:
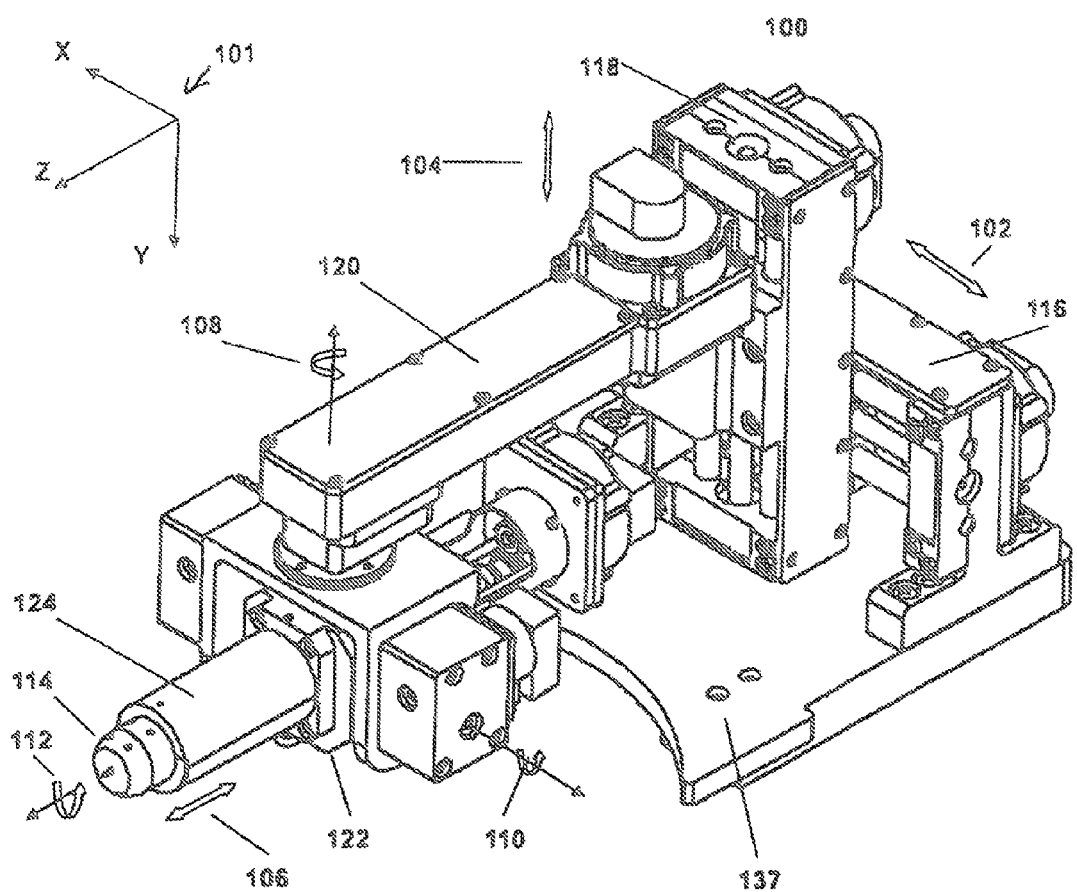
FIG. 14 is a perspective view of an alternate embodiment of a medical robot of the present invention having a medical instrument assembly positioned thereon.

The six degree of freedom medical robot 100 is used to automatically locate (orientation and position) the medical instrument assembly or trocar 124. The robot has three linear motion joints (horizontal, vertical and needle penetration) and three rotational joints (pan, tilt and roll). Arrows on FIG. 14 show the horizontal translation 102, vertical translation 104, needle penetration 106, pan 108, tilt 110 and roll 112. In addition the robot 100 may include a calibration phantom 114. The actuators are ultrasonic motors that being retentive can lock the needle into position so that no motor brakes are needed. FIG. 14 provides a schematic overview and FIG. 15 provides an exploded view of the robot 100.

Figure 15:
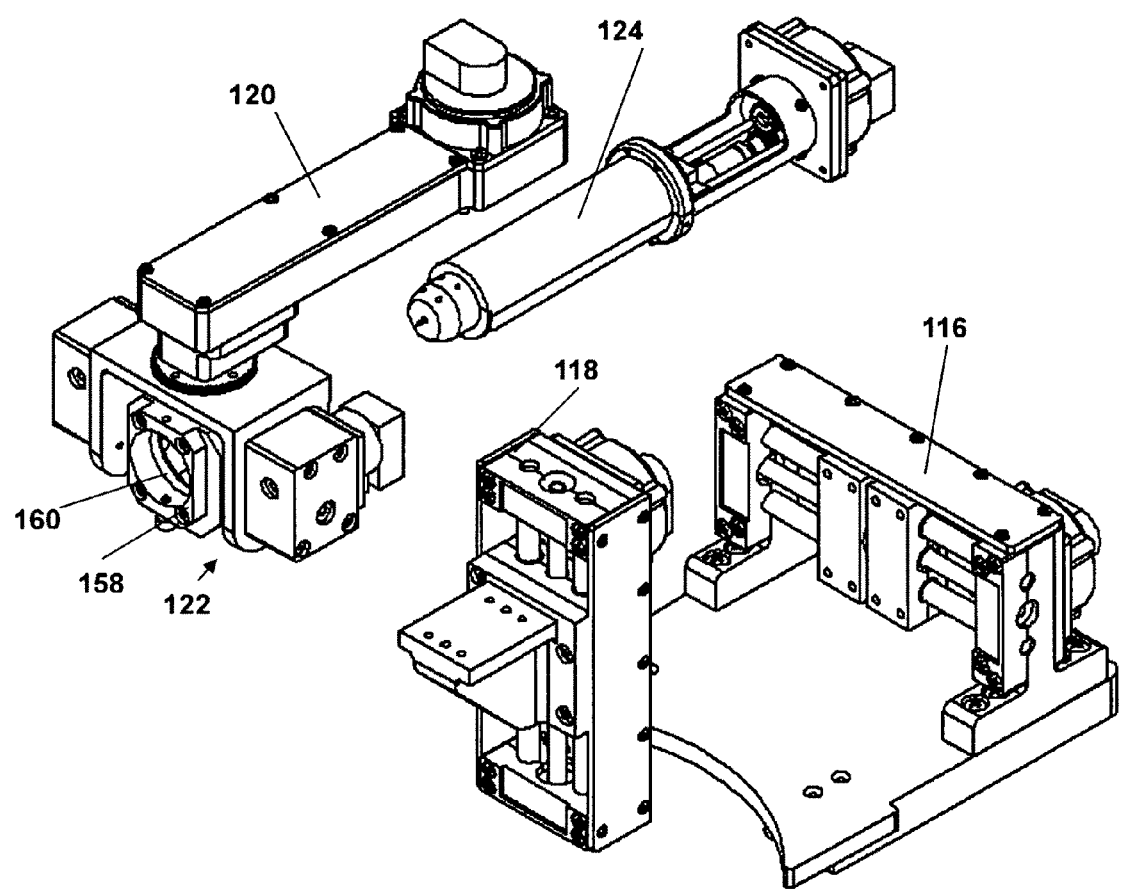
FIG. 15 is a partially blown apart perspective view of the medical robot and medical instrument assembly of FIG. 14.

As best seen in FIG. 15, robot 100 includes a horizontal translation unit 116, a vertical translation unit 118, pan unit 120, tilt and roll unit 122, needle penetration unit 124 and a calibration phantom 114.

Figure 16:
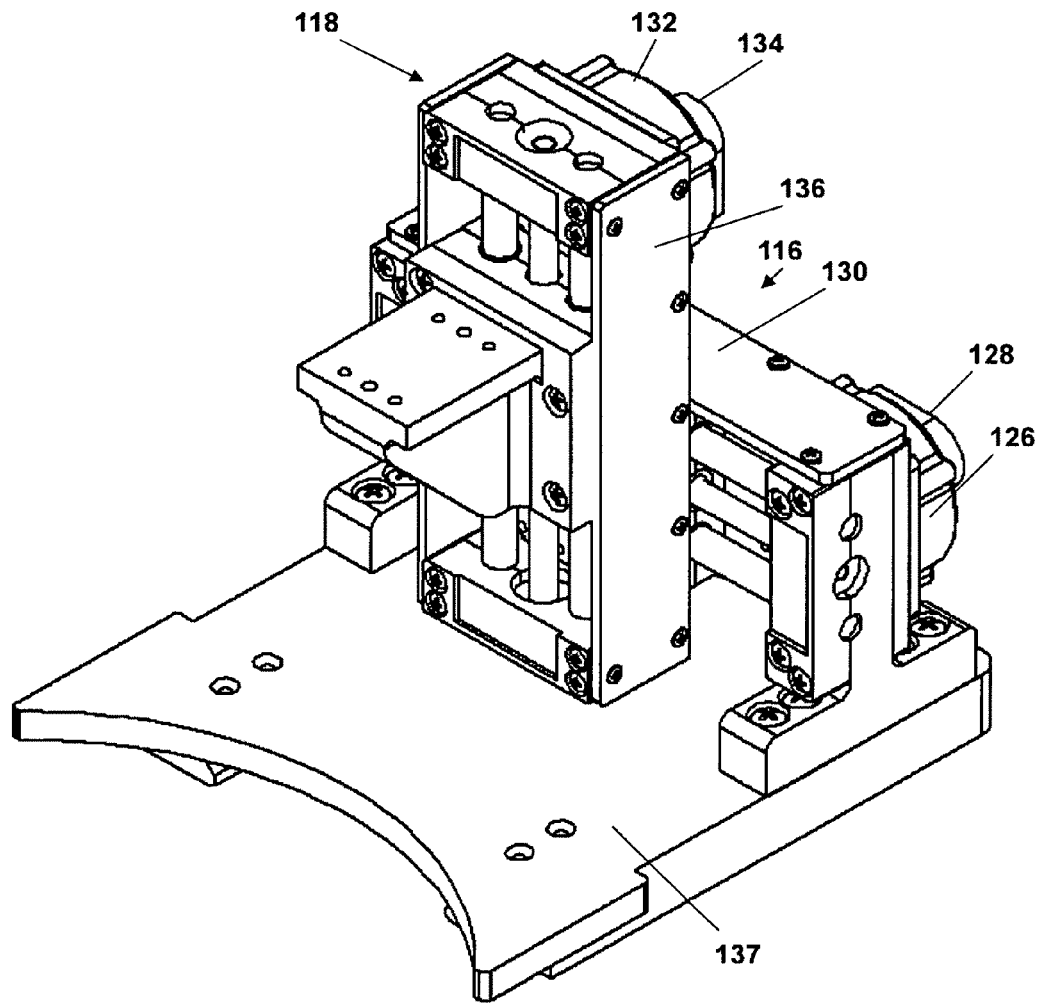
FIG. 16 is a perspective view of the horizontal and vertical linear motion portions of the medical robot of the medical robot of FIG. 14.

The robot has two separate linear motion joints to implement horizontal and vertical translations, respectively. FIG. 16 shows the structure of the robot base that translates horizontally and vertically. The horizontal motion unit 116 includes an ultrasonic motor 126 with an encoder 128 and a linear slide table 130. The vertical motion unit 118 consists of an ultrasonic motor 132 with an encoder 134 and a linear slide table 136. The vertical motion unit 118 is attached to the horizontal motion unit 116. Preferably ultrasonic motors 126 and 132 are USR60-E3N motors. The parts in horizontal motion unit 116 and vertical motion unit 118 are made out of the MR compatible materials. The horizontal motion unit 116 is attached to a base 137. Base 137 is shaped to accommodate coils used in association with an MR scanner. Specifically base 137 has an arcuate end to accommodate an endorectal coil (not shown).

Figure 17:
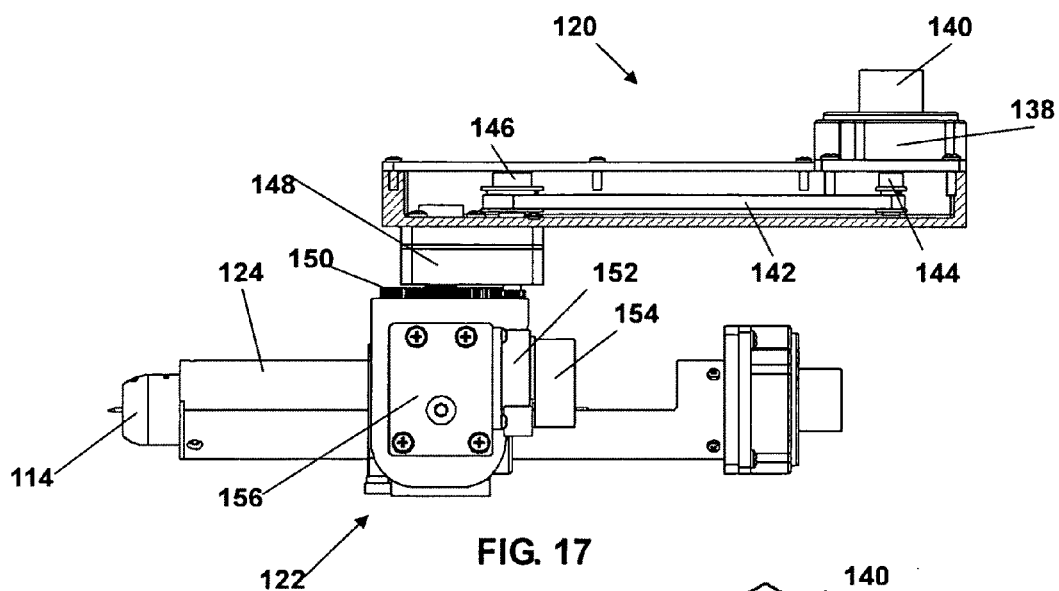
FIG. 17 is a side view of the pan tilt and rotational portions of the medical robot of the medical robot and medical instrument assembly of FIG. 14.
Figure 18:
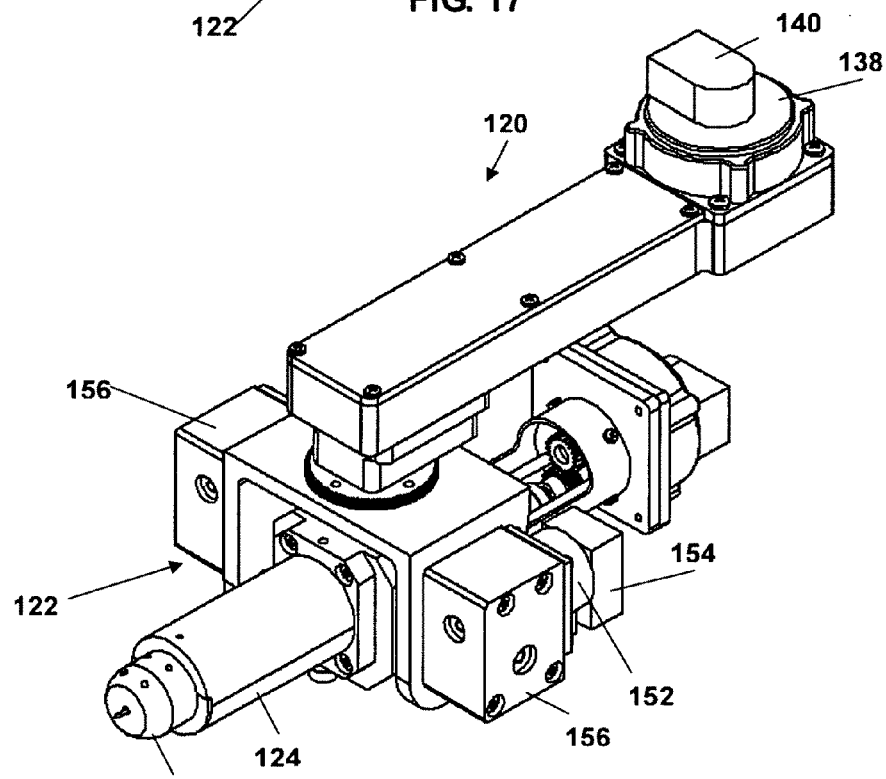
FIG. 18 is a perspective view of the pan tilt and rotational portions of the medical robot of the medical robot of the medical robot and medical instrument assembly of FIG. 14.
Figure 19:
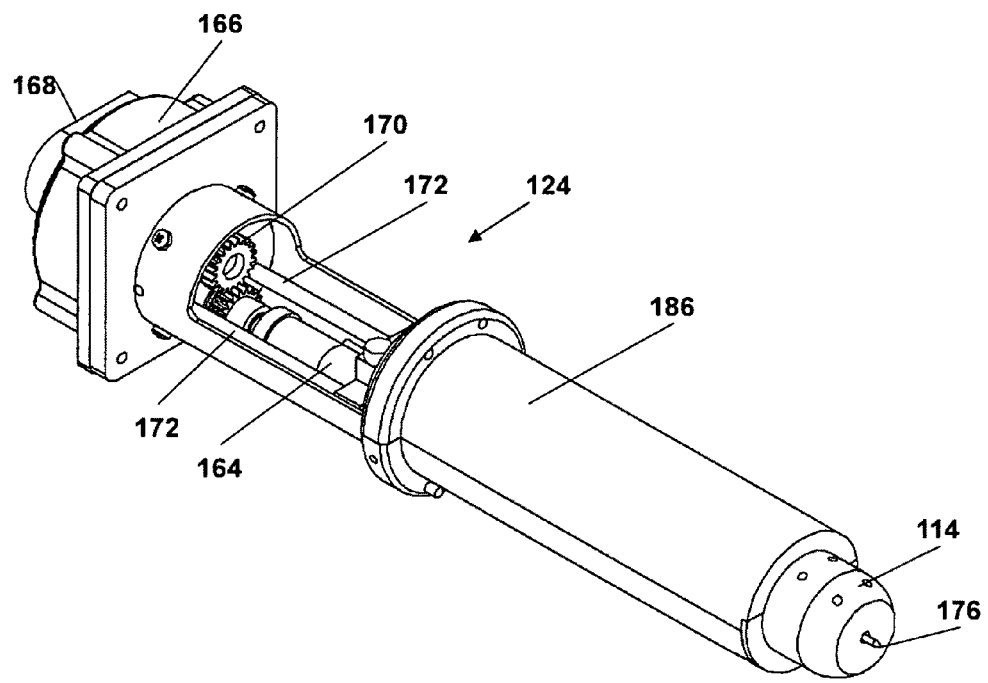
FIG. 19 is a perspective view of an alternate embodiment of the medical instrument assembly or trocar that is attachable to the medical robot of the present invention.
Figure 20:
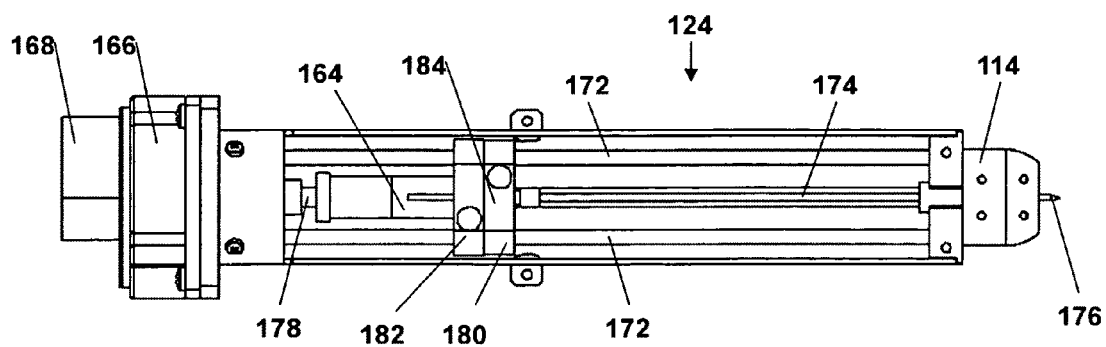
FIG. 20 is a top view of the medical instrument assembly of FIG. 19.
Figure 21:
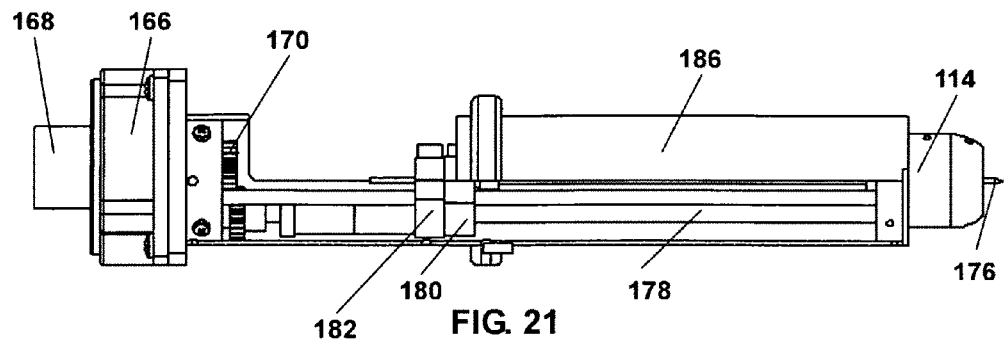
FIG. 21 is a side view of the medical instrument assembly of FIG. 19.

The robot has three rotation joints: pan 108 (rotation in horizontal plane), tilt 110 (elevation in vertical plane) and roll 112 (rotation), shown in FIGS. 17, 18 and 20. The pan unit 120 consists of an ultrasonic motor 138 (preferably USR60-E3N) with encoder 140, a timing belt 142 and pulleys 144 and 146, a pan shaft assembly 148 and a pair of gears 150. The tilt and roll unit 122 is composed of two ultrasonic motors 152 (preferably USR30-E3N) with encoders 154, two worm gear reducers 156 and a bevel gears differential mechanism 158. The transmission is from motors 152 to worm gear reducer 156, then to smaller driving bevel gears (not shown) and then to larger driven bevel gears 160. When the two driving bevel gears rotate at same speed and same direction, the tilting movement is realized; and when they rotate at same speed and reverse direction, the rolling movement is realized. Because the two motors work together, a larger torque output is obtained.

The penetration unit or trocar module 124 for laser ablation is shown in figures 17 to 24. The penetration unit 124 consists of the main parts: "needle" (or "trocar") tool; pushing & pulling mechanism 164; ultrasonic motor 166 (preferably USR60-E3N) with encoder 168, gears 170, guiding shafts 172, and a calibration phantom 114.

The "needle" tool consists of a titanium (or nitilon) needle 174 and a water cooled power laser applicator 176 which protects or cools the laser diffuser. The pushing & pulling mechanism 164, which comprises a lead screw 178, an insertion unit 180, the holder unit 182 for an irrigated power laser applicator, and a needle locker 184, is adapted to push the needle with the laser applicator tools to the target and the retract the needle for exposing the laser diffuser tip. And it is adapted to pull the "needle" tool back after the surgical operation is done. Accordingly the pushing and pulling mechanism provides linear motion and is the sixth degree of freedom for the medical robot 100. The lead screw 178 is equipped with a pair of ceramic ball bearings. The penetration unit includes a cover 186.

Figure 22:
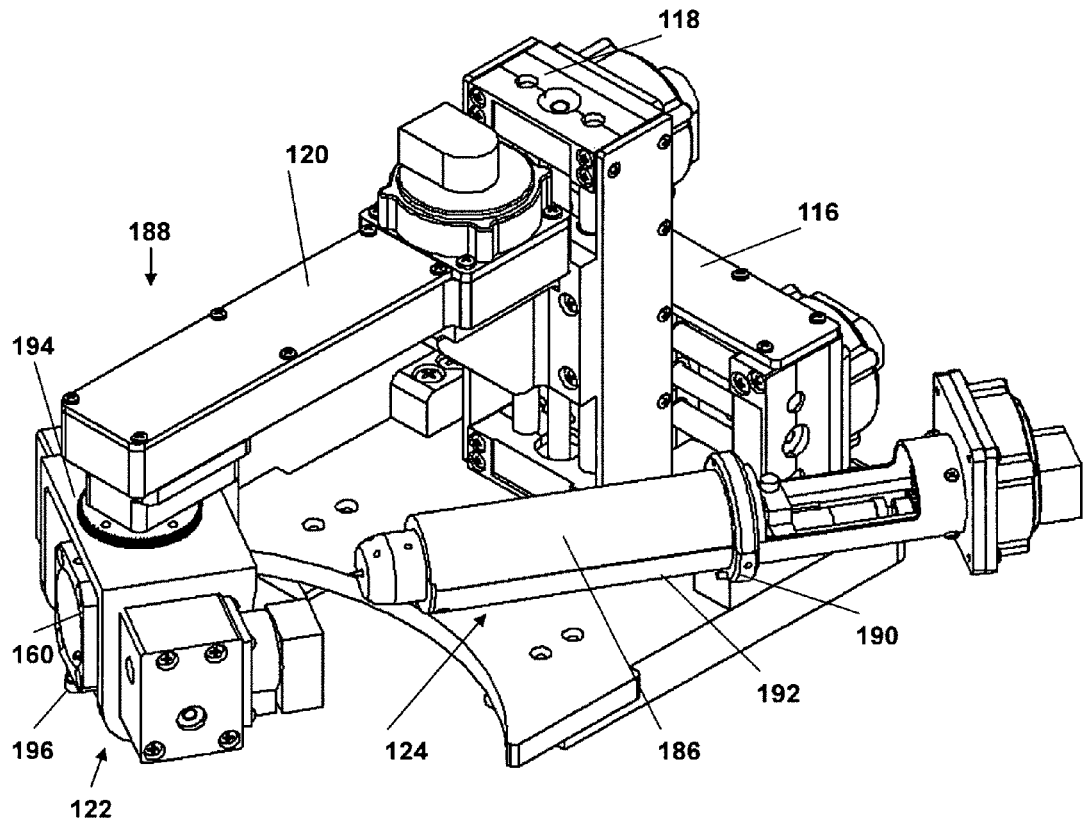
FIG. 22 is a perspective view of the medical robot of the medical robot of the medical robot of FIG. 14 with the medical instrument assembly ready to be attached thereto.
Figure 23:
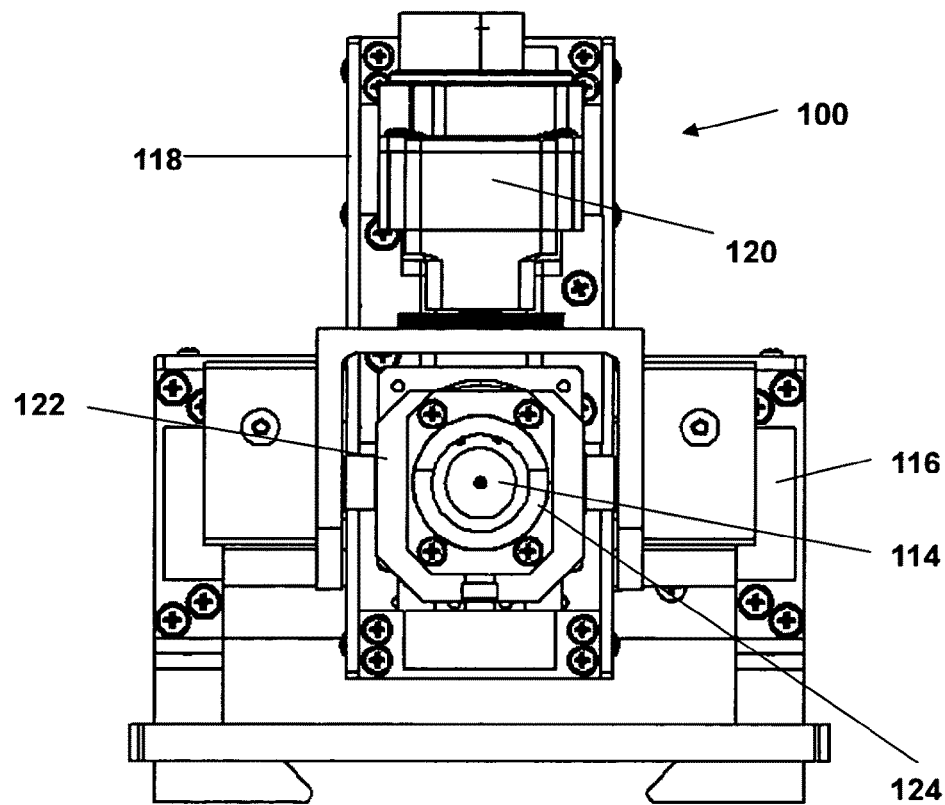
FIG. 23 is a front view of the medical robot with the medical instrument assembly attached thereto of the medical robot of the medical robot and medical instrument assembly of FIG. 14.
Figure 24:
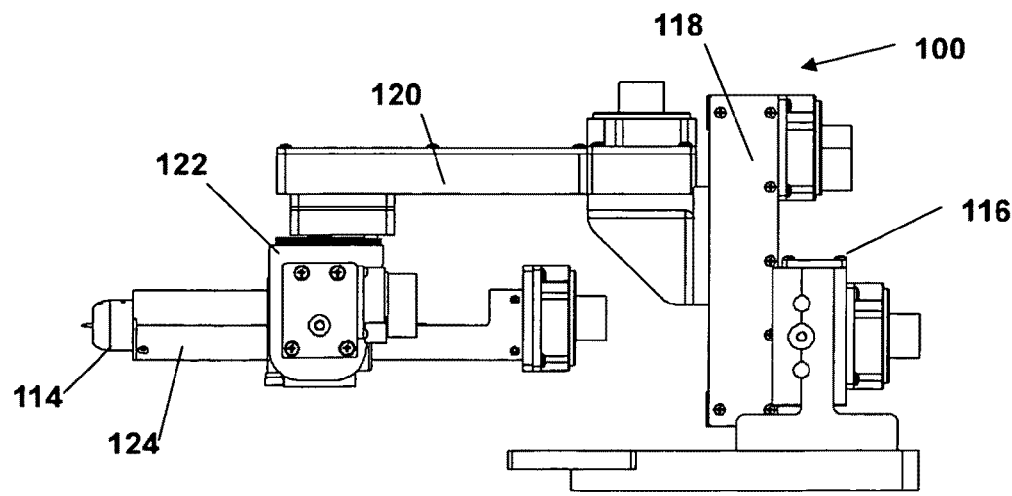
FIG. 24 is a side view of the medical robot with the medical instrument assembly attached thereto of the medical robot of the medical robot and medical instrument assembly of FIG. 14.

FIG. 22 provides an overview of the medical robot 100 with trocar modularity such that the robot can be considered as divided into two units, specifically a five primary DOFs base unit 188; and trocar module for laser ablation 124. Other trocar modules could also be used. For example trocars for biopsy and brachytherapy could also be used.

In order to allow the operator easily and quickly to substitute the trocar modules without having to make adjustments to the base unit, simple interfaces between the base unit 188 and the trocar module 124 are provided. A positioning block 190 with two pins is attached under the shell 192 of each trocar module 124 as shown in FIG. 22. By plugging the shell 192 of the trocar module 124 into the hollow of the support block 194 that is coupled with a large hollow bevel gear 160 on the base unit 188, and providing the positioning block 190 against the rear side of the support block 194, then locking with a thumb screw 196 the trocar module 124 can be quickly mounted on the base unit. After unlocking with the thumb screw 196 and being pulled, the trocar module 124 can be easily removed from the base unit 188.

Figure 25:
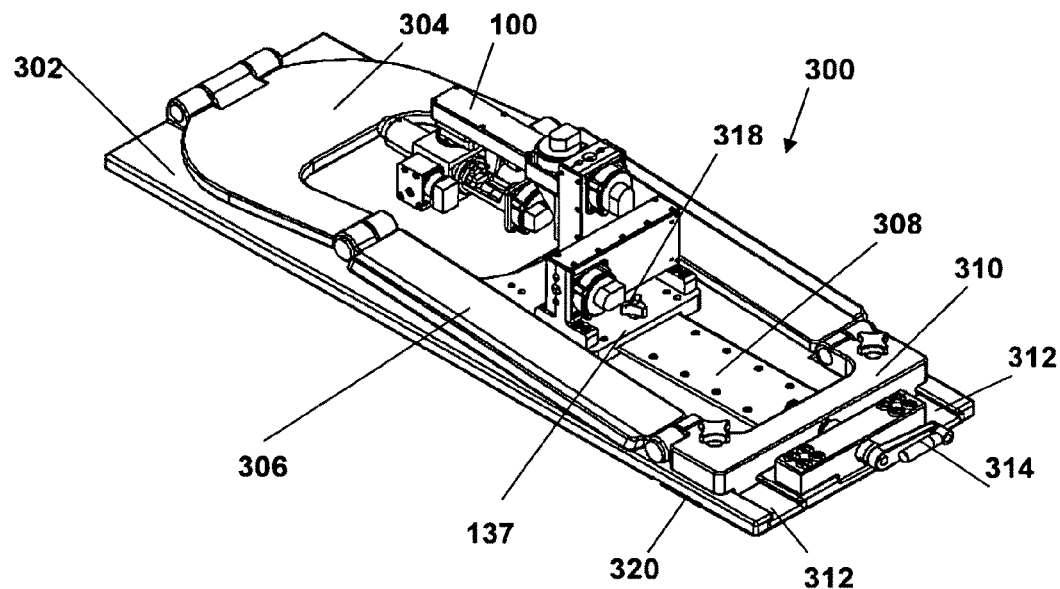
FIG. 25 is a perspective view of a platform that provides support for a patient and having the medical robot of the present invention attached thereto.
Figure 26:
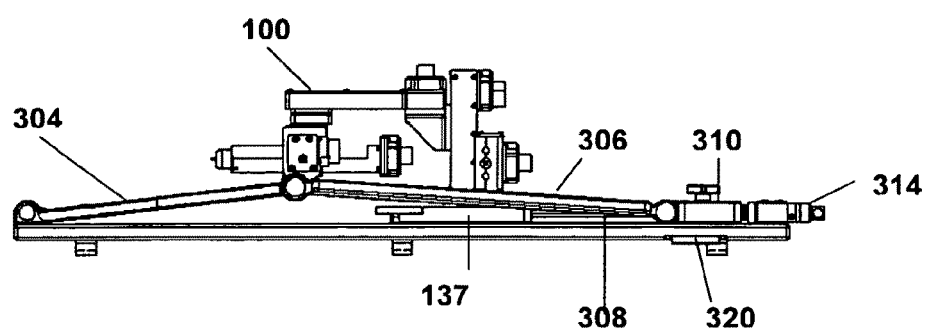
FIG. 26 is a side view of the platform of FIG. 25 with the medical robot of the present invention attached thereto.
Figure 27:
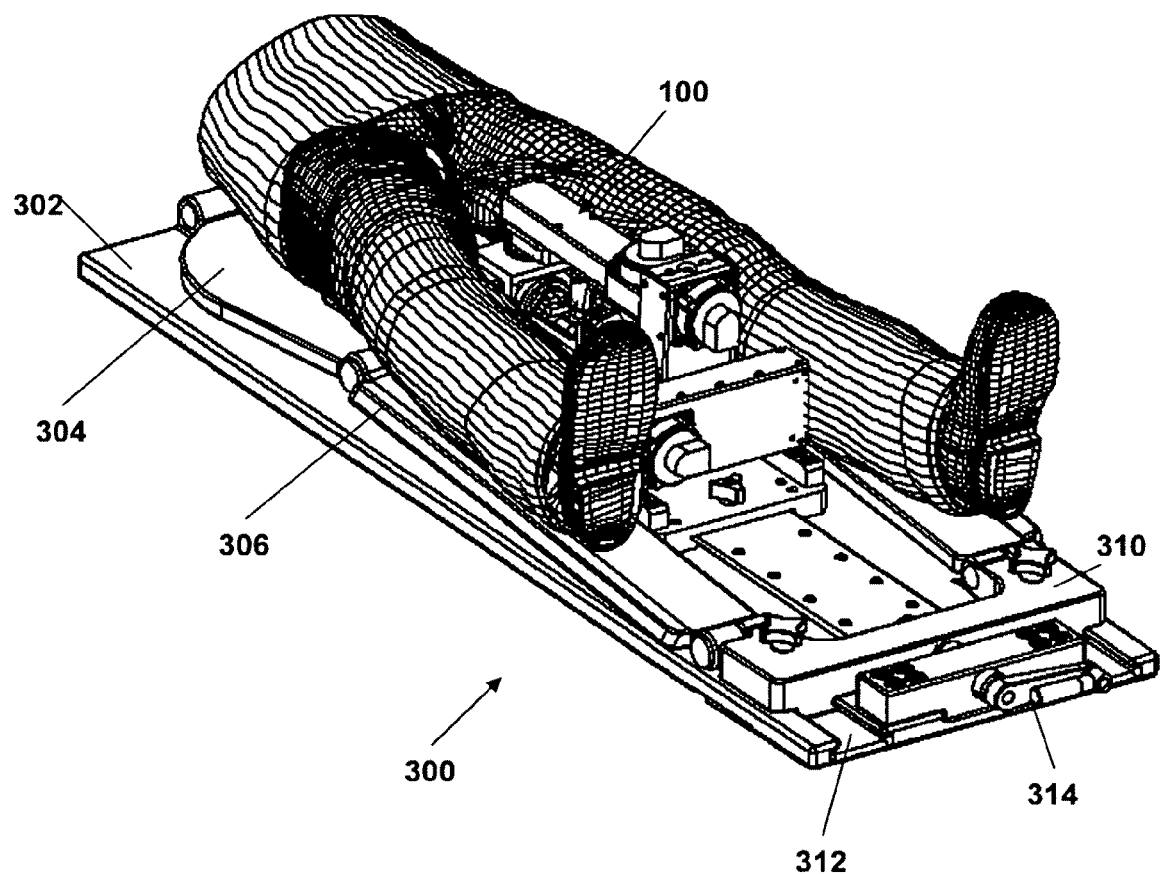
FIG. 27 is a perspective view similar to that shown in FIG. 25 but showing the lower portion of a person positioned thereon.

A platform that provides support for the patient and is adapted to have the medical robot 100 attached thereto is shown generally at 300 in FIGS. 25 to 27. The platform 300 has a patient receiving portion which includes a base plate 302, a haunch support 304, and a pair of leg support 306, and a robot guide 308 adapted to receive the medical robot.

The haunch support 304 is hingeably attached to the base plate 302 at one end thereof. The haunch support 304 is generally C shaped with two ends which are attached to the pair of leg supports 306. The pair of leg supports are hingeably attached to an adjustable mechanism assembly 310. The adjustable mechanism 310 slides along guide slots 312 at each side thereof. Reversible wrench 314 moved the adjustable mechanism assembly backwards and forwards along the base plate 302. In use, the haunch support 304 and leg supports can be adjusted so that the pelvis of the patient is positioned at the appropriate angle.

The medical robot 100 base 137 is shaped to fit over robot guide 308. The robot guide 308 is generally a wedge shape. Knob 318 holds the robot 100 in place.

The platform 300 is adapted to be used with a patient transport device (not shown). A plurality of positioners 320 are provided on the underside of platform 300 and are adapted to engage the patient transport device.

It will be appreciated by those skilled in the art that the platform described herein is by way of example only and it provides features that may be adapted to other types of surgery. Specifically the platform provides a device for adjustably positioning the patient and moveably secure a medical robot thereto. The device is designed to be adjusted manually. The platform is made from MRI compatible materials.

As discussed above, the major function of the robot is to deliver a medical device to a specified location. Further it is important that the robot functions well within the MRI. It was determined that the rotational speed of the robot could impact the accuracy of the robot inside the MRI. According to Maxwell's Equations, the faster the rotational movement, the greater the electromagnetic interaction between the robot and the main magnetic field of the MRI scanner. Therefore, the rotational robotic motion was reduced to reduce the robot-MRI electromagnetic interaction. Medical robot 100 uses a gearing mechanism to reduce the rotational robotic motion. However, other methods of achieving the same result are also possible.

Another potential manifestation of the electromagnetic interaction between the robot and the MRI environment is the production of eddy currents. These are electrical currents which are generated in conducting structures by a time-varying magnetic field. The presence of eddy currents can significantly degrade the quality of MR images. Accordingly, it is preferred that the presence of conducting surfaces and structures is minimized and ideally reduced to zero. Currently based on equipment that is readily available the source of eddy currents are the motors and to a lesser extent the encoders. However, it will be appreciated that as ultrasonic motors and encoders are developed which reduce or eliminate conducting these will be used. In the MRI environment, time-varying magnetic fields are present due to both radiofrequency (RF) waves as well as time-varying linear magnetic field gradients. To a good approximation, the RF and gradient processes occur in orthogonal orientations. This implies that if it were possible to orient the motors of the robot in a preferred orientation, the eddy currents caused by either the gradients or the RF could be minimized. Specifically, if the motors lie in the axial plane, the RF-induced eddy-currents could be minimized, while if the motors lie in the sagittal plane, the gradient-induced eddy currents could be minimized. The x, y and z planes of a MR imager is shown generally at 101 in FIG. 14. The axial plane is defined by the vertical or y axis and the sagittal plane is defined by the lateral or Z axis. As can be seen in FIG. 14 medical robot 100 has the cross sections of its motors oriented in the axial and sagittal planes.

In the MRI environment, there are a number of possible sources of electromagnetic interaction with the robot. One of the major potential sources is the local coils that collect the data used to form the MR images. Typically, these local coils are constructed in a manner that creates a close spatial conformation with the anatomy that is being imaged. For example, when imaging the brain, a local coil that resembles a helmet is typically used. A method that would minimize the electromagnetic interaction with the robot and the local coils is to physically separate the conducting structures of the robot from the local coils. In the present invention, the robot motors are positioned a specified distance (or greater) from the local coils. For example, in the case of the head coil, the robot motors could be placed at the chest level. By way of example only in the embodiment herein the US motors (USR60-E3N) should be placed around 30 cm or more away from the front of the robot, and preferably in an axial orientation. The smaller motor (USR60-E3N) could be placed less than 30 cm when they are placed in an axial orientation.

The MRI scanning operation generates EMI noise that affects the encoder, and this noise causes inaccurate position feedback readings. In parallel, the ultrasonic motor (U/S) operation generates EMI noise that affects the clarity of MR images. It was determined that the processor (controller) generates the latter effect, as well as facilitates the former.

After testing several methods to avoid these effects it has been determined that a "power on/off" solution is the best solution. Specifically, it has been determined that turning the controller power (3.3V) on and off, while maintaining the U/S power (24V), and encoder power (12V) on, suffices in not generating significant EMI, thus acceptable MR images and noiseless encoder readings are produced. Table 1 shows the effect the different power sources have on the MR images. Accordingly it is an unexpected result that the device with the lowest power causes the distortion in the images.

TABLE 1

| Scan # | Power issue | Distance ** | Cables connection | Image Artifact | Noise (on image) |
|---|---|---|---|---|---|
| 1 | All power * Off | 15 cm *** to 20 cm | Motors with cables & encoders with cables | No | No |
| 2 | All power * On | 15 cm *** to 20 cm | Motors with cables & encoders with cables | No | Significant RF noise |
| 3 | 24 V power On 3.3 V & 12 V Off | 15 cm *** to 20 cm | Motors with cables & encoders with cables | No | No |
| 4 | 3.3 V power On 24 V &12 V Off | 15 cm *** to 20 cm | Motors with cables & encoders with cables | No | RF noise |
| 5 | All power * On | 15 cm *** to 20 cm | Motors without cables & encoders without cables; all cables are outside the bore | No | No |
| 6 | All power off | 0 cm *** | Motors with cables & encoders with cables | Yes | NO |

* Power: DC 24 V, 12 V and 3.3 V
** Distance: the distance between the motors on the robot closest to MR scanner isocenter and the scanner isocenter
*** Consider all motors within_50 cm In order to store the data of the robot current position when the controller power is off, a backup battery is used in the controller to keep up the current position data in the processor SRAM. A USB device that has A/D digital I/O and some relays are included to switch the power on and off very rapidly.

The control system architecture of the MRI-P is master-slave (decentralized architecture). This helps control accurately the motor position and speed control.

Figure 28:
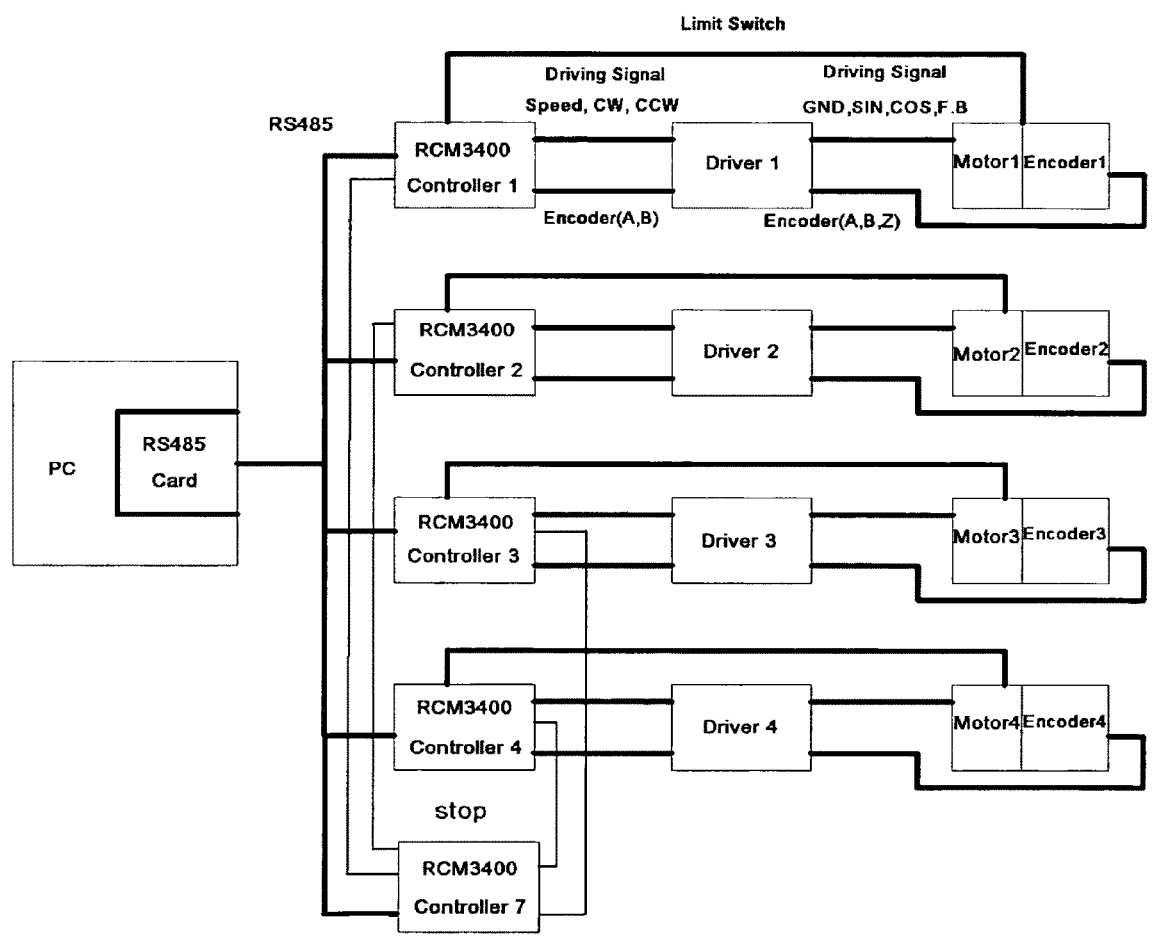
FIG. 28 is a schematic diagram of the control system of the medical robot of the present invention.

In contrast in most reported prior art applications of MRI-based U/S motor control, a centralized architecture is adopted. A decentralized architecture is used herein, with one Rabbit processor RCM3410 controlling one motor (FIG. 28). The master controller receives user's commands, and sends the commands to salve controller via RS485 bus and custom protocol.

Some time the user may want to stop the motion instantly. But in normal motion control mode, the controller is busy on checking the position feedback synchronously, and cannot receive commands. A separate RCM3410 board to communicate with the master controller was included to provide the user with this capability. When the separate controller receives the stop command from the RS485 bus, it sends a digital signal to the targeted joint controller to instantly stop the motion.

The communication protocol provides communication between master and slave controllers. There are two kinds of frame in the protocol: short frame and long frame. Long frame is 13 bytes long: it transfers motion parameters from master to slave such as desired speed and target position; it also transfers feedback of current position from slave to master. Short frame is 6 bytes long; it transfers short commands without parameters for fast communication. The main purpose of these protocols is to speed up the process in order to increase the speed of robot operation.

The speed of robot operation is a crucial issue in acceptance by the medical community. The need to turn the controller on and off slows down the operation. There is a need to optimize the process. Note that this only relevant in regard to the trocar motor (linear motion) because the robot's other joints are positioned prior to insertion, when the trocar is outside the body.

The motor on/off cycle is divided into the following periods:
UP: time required to reset and initialize the controller after OFF;
ON: time the motor is running (controller is ON);
DOWN: time required to turn OFF the controller;
SCAN: time required to scan, during which the controller is OFF.

The values considered at this time are: UP—0.3 s; ON—depends on the required average velocity over the cycle; DOWN—0.01 s; SCAN—0.3 s. The maximum speed of the linear motor is 15.885 mm/s. Thus, for example if ON is 0.39 s (cycle=1 s) the average velocity over the cycle is 6.19 mm/s.

The objective here is to minimize the UP and DOWN time by hardware and software design. The ON and SCAN are set by the user. Ideally the total of UP and DOWN should be minimal to boost up the speed.

Another method to increase the average velocity is to change a mechanical part, for example lead of the screw for the penetration joint. The lead may be increased by 2 or 4 times. This would increase the maximum speed 2 to 4 times. But it will also reduce the penetration force 2 to 4 times, which is not desirable.

Figure 29:
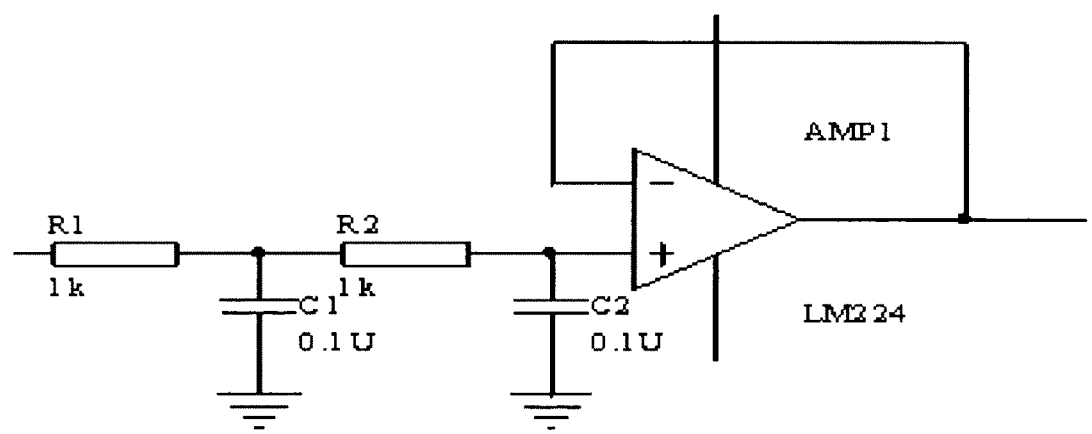
FIG. 29 is a circuit diagram to transform the digital signal of the RCM into an analog signal for the driver.

The driver USR60 E3N made by the motor manufacturer provides accurate speed control. The driver gets the speed feedback form the encoder, and adjusts the output current to the motor to control the motion speed. The speed control accuracy is guaranteed by the manufacturer. The speed loop is closed on the driver. The only issue is that the driver of USR60 requires an analog signal, but the RCM only outputs digital signals. A circuit which transforms the PWM output of the RCM into an analog signal to the driver is shown in FIG. 29.

A sensor is used for homing procedure of each joint. During the homing the sensor is providing a reference position. This signal is highly repeatable. When a homing command is generated, the motor is moved in a pre-defined direction, while checking the sensor signal. When the signal is detected, it implies that the motor has touched the reference position, and the motor stops immediately. Then it is driven to a pre-defined position, that is the 'home'.

For pan and tilt joints, they are driven by two interfaced controllers, and only one controller can receive the signal from the sensor, this receiving controller will provide the other controller a digital signal synchronously.

Figure 30:
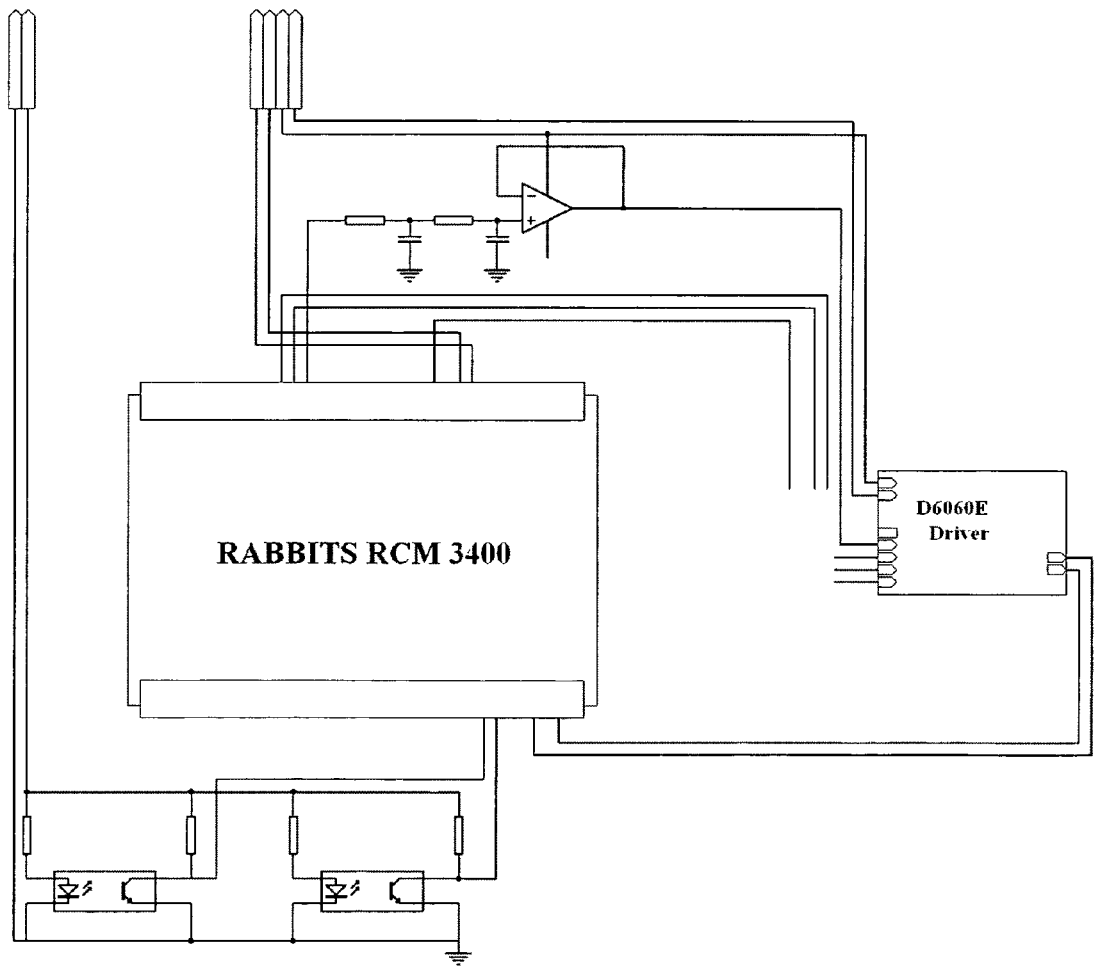
FIG. 30 is a circuit diagram of the motion control system.
Figure 31:
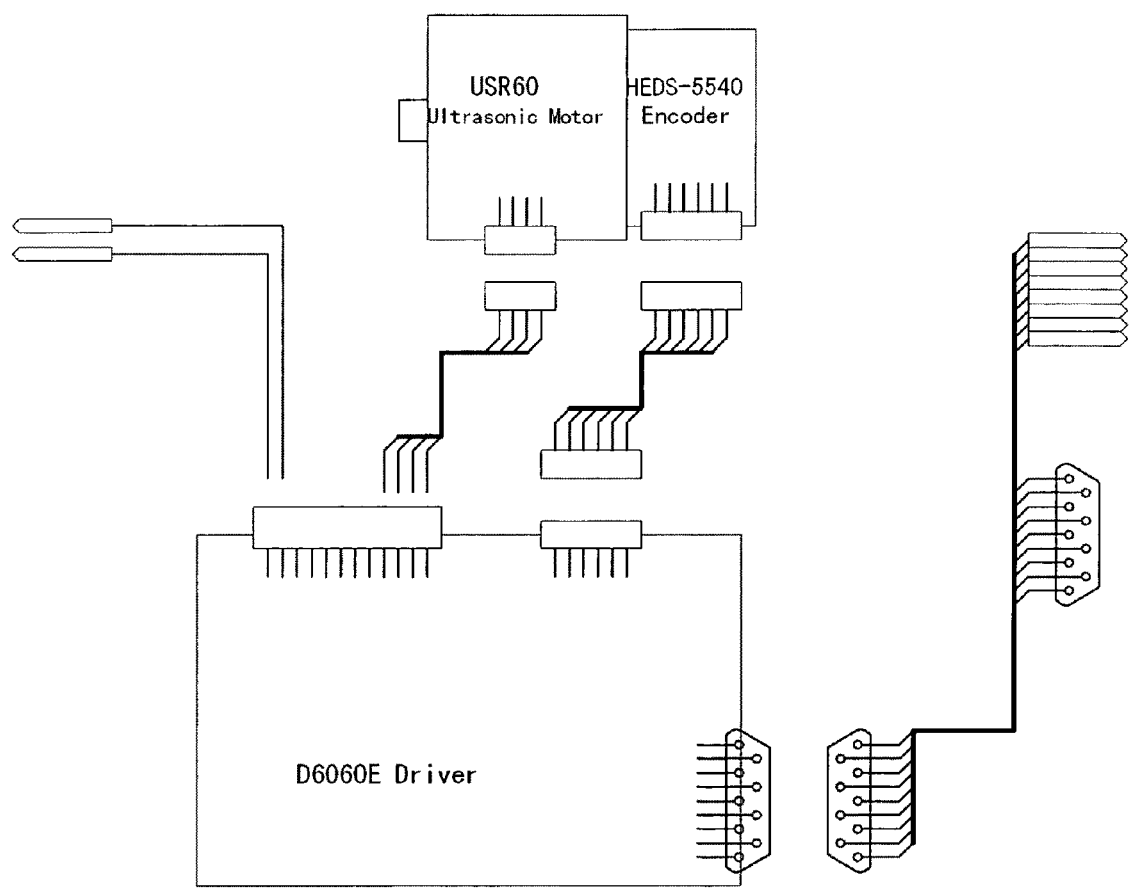
FIG. 31 is a circuit diagram of another motion control system.

Preferably the control system herein is a closed loop position control on the slave for each U/S. FIGS. 30 and 31 show the architecture of this motion control system. The controller sets the speed and motion direction for the driver. The minimum speed of this type of ultrasound motor is 15 rpm (for joint 1 is 30 rpm because it uses a different model of motor). It means that the motor will move at 15 rpm speed even when the speed is set to zero. This characteristic restricts the use of regular control algorithms such as PID.

Figure 32:
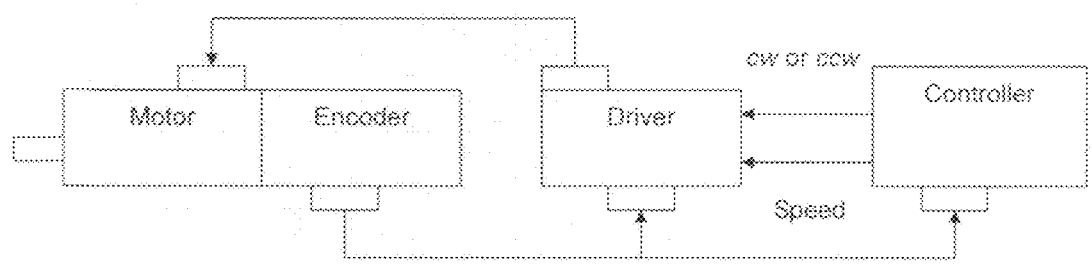
FIG. 32 is a block diagram of the motion control of each joint in the medical robot and medical instrument assembly.

The U/S motor is designed to stop as closed to instantly and precisely as possible. The motion sensor is 500 lines quadrature encoder. This implies that the error (1 count) is 0.18 degree for each joint. The motion control block diagram is shown in FIG. 32.

When a motion command is received, the controller will send the motion direction and speed to the driver. Then the controller will check the motor position continuously. When the motor is closed to the commanded position (within 300 counts), the controller decreases the speed. While it moves into the right position, the controller stops the motor immediately.

In order to use the images generated by the MRI scanner to guide the robot to a specified location, it is necessary to synchronize the coordinate systems of the robot and the MR scanner. In our system, this is accomplished by acquiring an MR image while the robot is at a specific, known location. The position of the robot in the MR images is then identified. With the MR-derived and robot-known positions determined, the robot and MRI coordinate systems can then be synchronized. To employ this method, one major challenge that must be addressed is how best to identify the robot position in the MR images. In the present invention, three alternative methods for accomplishing this task are outlined below:

A needle is advanced by the robot to some known position inside an MR-visible object. The MR-visible object could be the human body, or some external test object (e.g. gel phantom). When placed in the MR-visible object, the needle will appear dark. In this manner, the position of the needle tip can then be visualized on an MR image.

Figure 39:
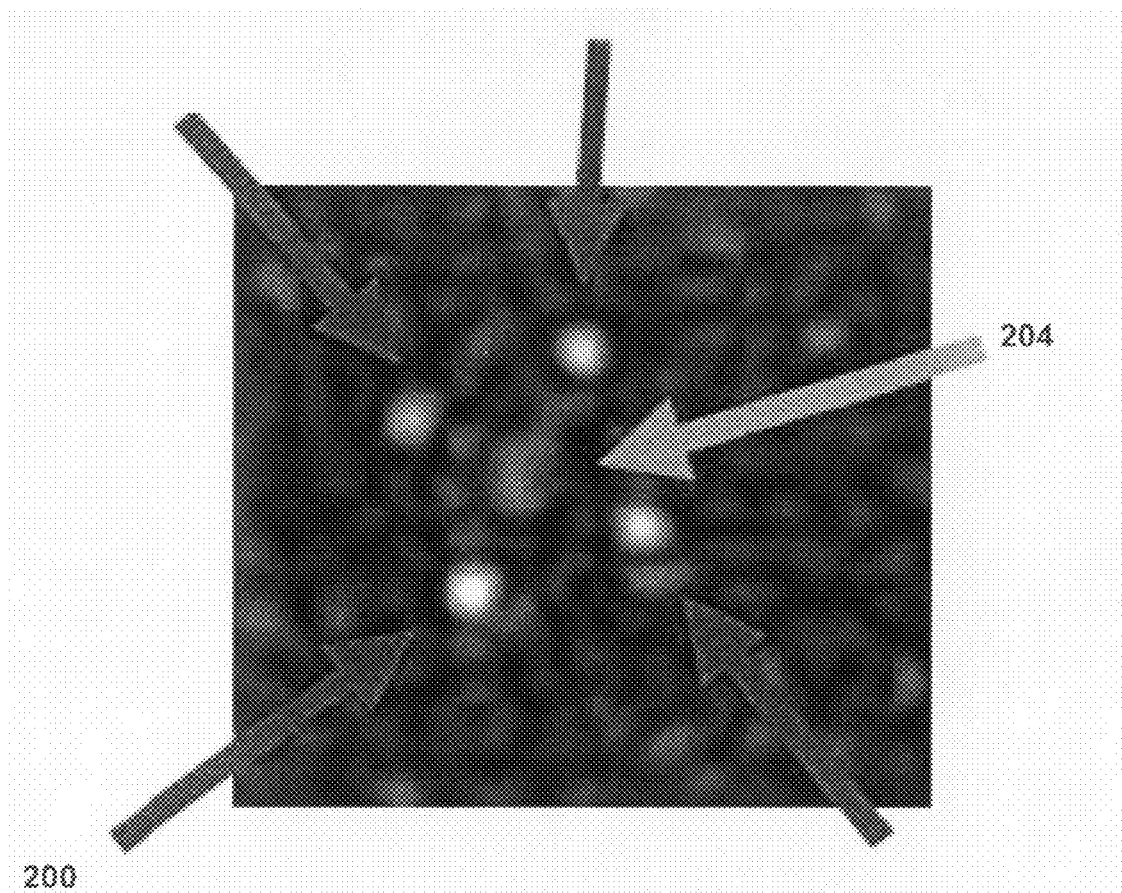
FIG. 39 is a magnetic resonance image of the calibration phantom of FIG. 34.

A calibration phantom is used that can indirectly provide the position of a needle tip on MR images. The calibration phantom consists of 4 water channels (see FIG. 33). The needle lies in the exact middle of all four channels. The needle position is determined as follows: First, the location of each water filled channel is determined on an MR image. Second, the centre point of the four needles is calculated from these locations (see FIG. 38). This procedure localizes the needle tip in two planes. A similar procedure is performed in an orthogonal plane to localize the needle position in the third dimension. FIG. 39 is an MR image of a prototype calibration phantom. In future robot designs, the calibration phantom may be incorporated directly into the robot itself.

The needle may be filled and/or surrounded by water (or contrast-agent-doped water). In this manner, the needle can be visualized on MR images.

Figure 33:
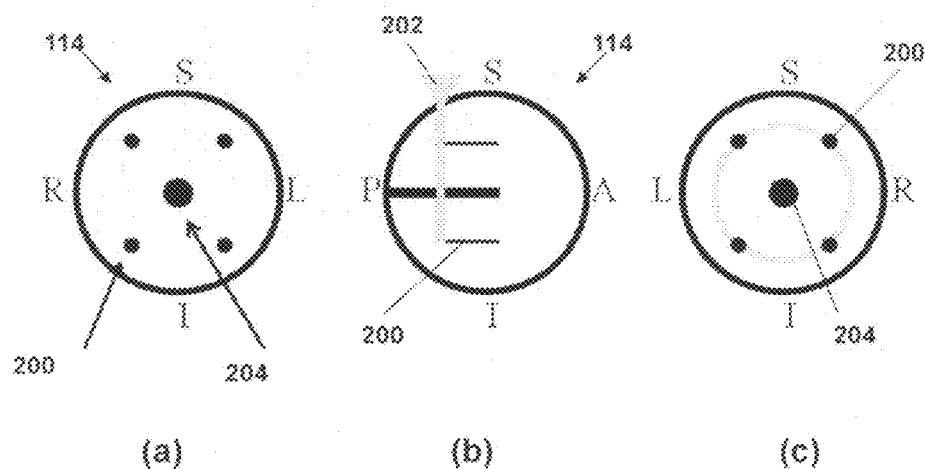
FIG. 33 is a schematic diagram of the calibration phantom for use in association with a medical instrument assembly with a) showing a front view, b) showing a side view and c) showing a back view.

More specifically, an embodiment of calibration phantom 114 including a schematic representation of the front a) side b) and back c) is shown in FIG. 33. The calibration phantom 114 is also shown in FIGS. 34 to 37. The calibration phantom 114 includes four water filled channels 200 and a filling port 202. The needle holder 204 is in the centre of the four channels 200. The calibration phantom includes a housing 201 that is attachable to a medical instrument. It will be appreciated by those skilled in the art that the calibration phantom 114 is shown attached to a specific trocar. However, it could be adapted to be used to locate any type of medical instrument wherein the channels are at a predetermined location to a point of interest in the particular medical instrument. In the example shown herein the point of the interest is the needle tip 202.

The calibration phantom 114 includes water-filled tubes 200 oriented in a manner such that a line drawn between the two will go through the needle tip 202 (see FIG. 38).

In calculating the location of the needle tip 202 it is assumed that there is effectively no error in the "true" position of the water-filled tubes. On the MR image, the position of the needle tip is calculated as follows:

1) The (x,y) position of a water-filled tube, together with the corresponding tube on the opposite side will be measured. The mid-point along a line drawn between these two tubes will correspond to the needle tip:

$$(x_{tip}^1, y_{tip}^1) = \left(\frac{1}{2}[x_a^1 + x_b^1], \frac{1}{2}[y_a^1 + y_b^1]\right)$$

The uncertainty in position of all measured points ($x_a^1$, $x_b^1$, $y_a^1$, $y_b^1$) will be the image resolution ($\delta$). This uncertainty can be considered as the standard deviation of a distribution about the true position of each point (the specific form of the distribution does not matter for this derivation, though it could be safely assumed to be Gaussian if necessary). It is assumed that the uncertainty in position of one measurement is uncorrelated with any other measurement (the validity of this assumption will be discussed later). Under these assumptions, it follows trivially from basic statistics that the standard deviation of $x_{tip}^1$ and $y_{tip}^1$ is $\delta/\sqrt{2}$.

2) Step #1 is repeated for all remaining n/2 pairs of tubes. The uncertainty in the estimate of needle tip position from each of these measurement is $$\left(x_{tip}^i, y_{tip}^i; i = 1 \ldots \frac{n}{2}\right)$$

is $\delta/\sqrt{2}$, as in step #1.

3) The average of all estimates of needle tip position is taken:

$$(x_{tip}^{av}, y_{tip}^{av}) = \frac{1}{n/2} \sum_{i=1}^{n/2} (x_{tip}^i, y_{tip}^i)$$

Since the standard deviation of each position is ($x_{tip}^i$, $y_{tip}^i$) is $\delta/\sqrt{2}$ and with the assumption that all of the ($x_{tip}^i, y_{tip}^i$) are uncorrelated, the standard deviation of ($x_{tip}^{av}, y_{tip}^{av}$) is therefore:

$$\frac{\delta/\sqrt{2}}{\sqrt{n/2}} = \frac{\delta}{\sqrt{n}}$$

This derivation is predicated on the assumption that all measurements of position are uncorrelated. This is likely true for all situations except the degenerate case where the water-filled tubes are aligned at 0 or 90 degrees. In this case, the tube position and the imaging grid will be aligned with each other, and the measurements will be correlated for either the x or y position. The solution to this is simply to avoid placing the water filled tubes at the 0 or 90 degrees position.

Figure 40:
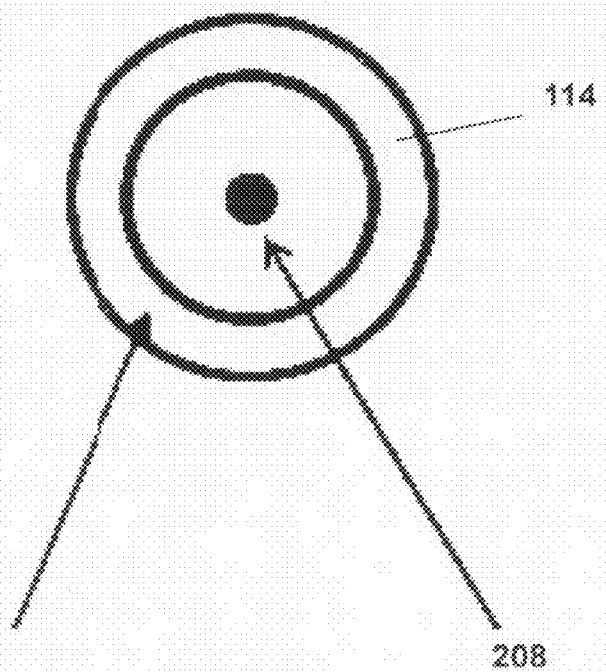
FIG. 40 is a schematic diagram of a front view of an alternate embodiment of the calibration phantom for use in association with a medical instrument assembly.

Alternatively the calibration phantom 114 may include an annular ring of water 206 and the needle tip 208 is calculated at the centre of the circle as shown in FIG. 40.

Figure 49:
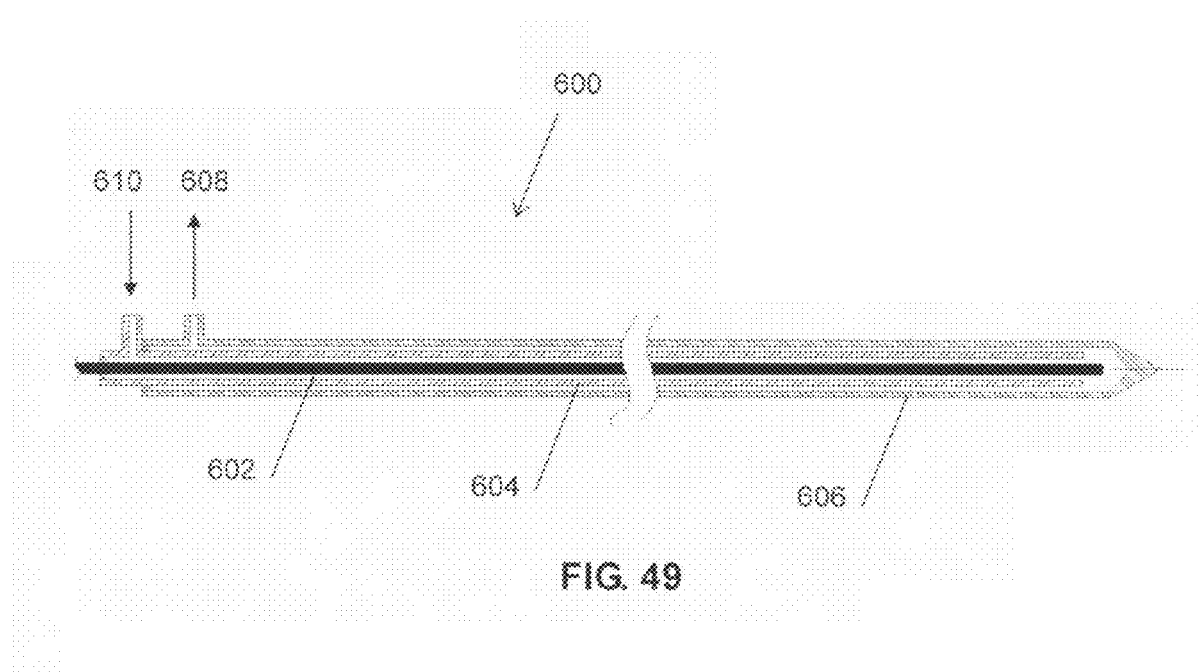
FIG. 49 is an enlarged cross sectional view of the laser applicator of an embodiment of the medical instrument.

Referring to FIG. 49 a laser applicator is shown generally at 600. Laser applicator 600 may be used in association medical instrument 12 shown in FIG. 1 and in detail in FIG. 6 to 8 or medical instrument 124 shown in FIG. 14 in detail in FIGS. 19 to 21. Laser applicator 600 includes a laser fiber 602 surrounded by an inner catheter 604 and an outer catheter 606. Inner catheter 604 is in flow communication with outer catheter 606. Outer catheter 606 has an outlet port 608 and inner catheter 604 has an inlet port 610. Catheters 604 and 606 has a mixture of water and an MRI visible fluid circulating therethrough. Preferably the MRI visible fluid is Gd (gadolinium) and the fluid includes between 10% and 1% Gd.

For some applications, it may be desirable for the robot and the MR scanner to exchange information and/or data with each other. The present invention proposes several methods of achieving this communication:

Images and/or data may be transferred between the robot and MR scanner via FTP.

Images may be transferred between the robot and the MR scanner via DICOM push/pull protocols Images and/or data may be transferred between the robot and MR scanner through the MR scanner's built-in real-time protocol (RTP).

Images and/or data may be transferred between the robot and MR scanner through a BiT3 device.

One particular application where robot/MRI communication may be essential is in real-time robotic visualization. In this application, MR data acquisition and robotic usage occur simultaneously. However, in cases where the electromagnetic coupling cannot be sufficiently suppressed, then the activation of the MR scanner and the robot could be interleaved. In this scenario, robotic usage and MR data acquisition are switched on and off in rapid succession to simulate real-time functionality and the on/off states of the MR scanner and the robot are co-ordinated. This coordination could be achieved by sending signals back and forth between the MR scanner and robot using one of the aforementioned data communication mechanisms. An additional method of achieving such communication could be via TTL signals.

Within an MRI imaging exam, a variety of different pulse sequences, and pulse sequence parameters may be used to affect the visualization of the object being imaged. The specific pulse sequence and parameters used for a particular application are typically chosen to optimize the visualization of the object. This optimization may include (but not limited to) maximizing signal-to-noise ratio (SNR), maximizing contrast-to-noise ratio (CNR), and minimizing artifacts. For the robotic application, a gradient echo pulse sequence with a short echo time (TE) was determined to provide a good visualization of the needle. When the needle and/or fibre was filled with Gadolinium contrast agent, a fast-spin-echo (FSE) pulse sequence with a short echo time was determined to provide a good visualization. For visualizing coagulation, three different pulse sequences are used: long-TE FSE, T1-weighted FSE, and short-TR gradient echo.

To monitor temperature in real-time with MRI, several methodologies had to be developed. First, a technique for converting MRI data into temperature elevation maps was implemented. This technique utilizes the phase of MRI images. Secondly, a technique for accessing the data in real-time was developed. In the current implementation, data was accessed via FTP. More generally, however, other methods including those outlined above are possible.

An anatomically correct MR compatible phantom suitable for focal interventions is useful in the design, development, testing and training of medical robots for use in an MRI.

Figure 41:
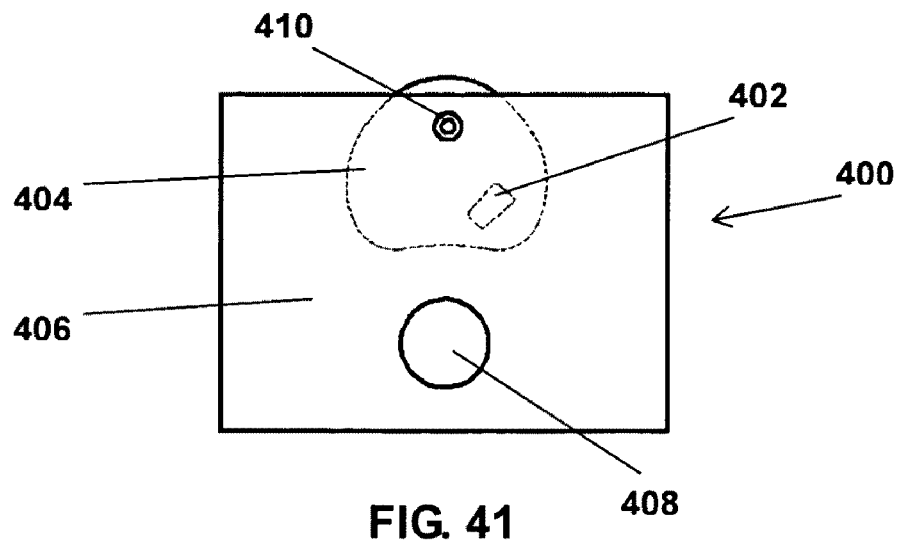
FIG. 41 is a front view of a prostate phantom for use in a magnetic resonance imager.
Figure 42:
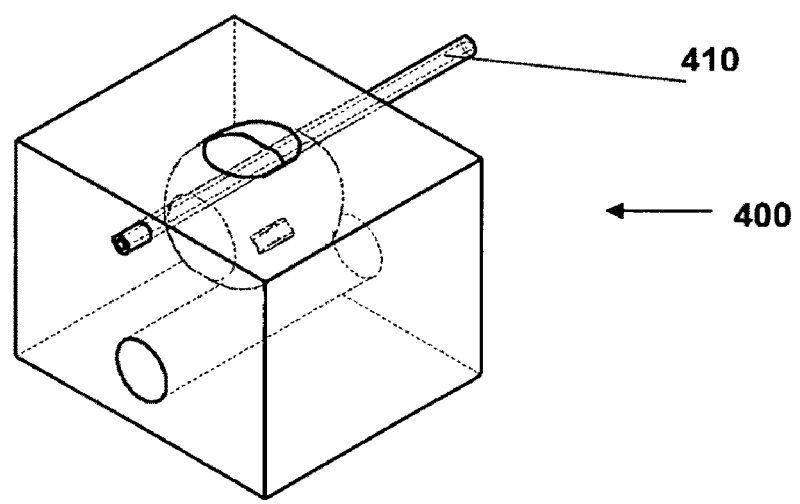
FIG. 42 is a perspective view of the prostate phantom of FIG. 41.
Figure 43:
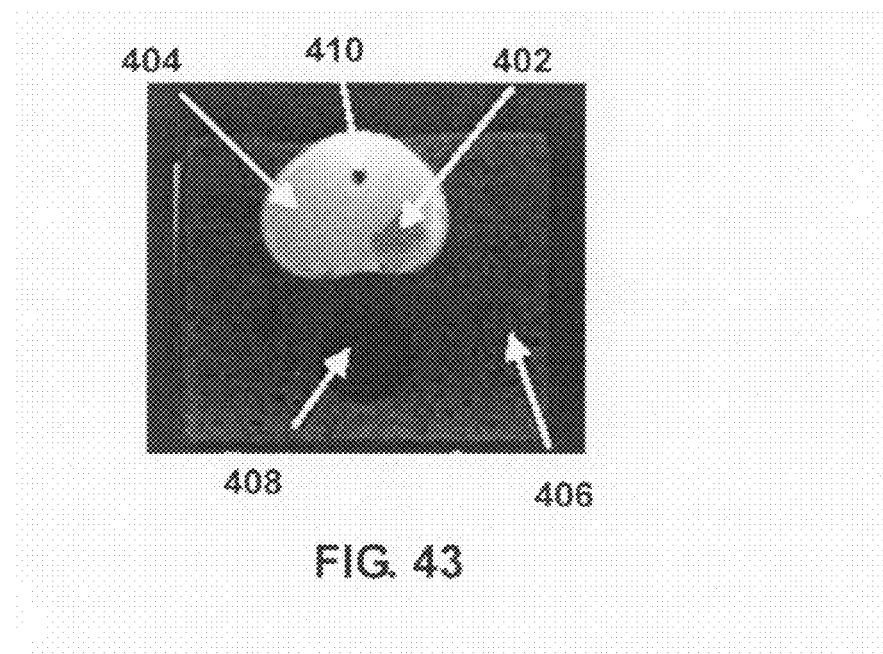
FIG. 43 is a magnetic resonance image of the prostate phantom of FIG. 41.

The phantom 400 shown herein in FIGS. 41 to 43 is designed to be anatomically correct, MR compatible and contain a part that would allow focal ablation. Phantom 400 includes a treatable portion 402 which in the example herein is approximately 5 cc, an anatomically correct "prostate" 404 and a perineum like structure 406 with "rectum" 408.

The treatable portion 402 varies according to focal intervention type. It is made of different shelf gels with different properties. The gel may be dye green and includes some intralipid fat and proteins that make it amendable to coagulation using laser energy. Alternatively a different gel may be used that makes it amendable to HIFU thermal energy. For example materials from ATS LAbratories Inc. may be used In the embodiment herein, the "prostate" 404 is made in a mold. The mold is a simple mold and can be made to any prostate size. The "prostate" is made from a gelatin that is commercially available in every supermarket with Gadolinium added to the mixture. The "urethra" 410 of the prostate is made from a Foley catheter.

The perineum like structure 406 is made in a cubical mold with an open top. The "rectum" 408 is created by using a tube in place while filling the mold. The material of the "perineum" is commercially available dental histomer. Once the lower part of the perineum is created, the "prostate" is placed on top and the mold is filled to encompass the prostate. By way of example Cavex CA37, Cavex CA37 Normal Set and CavexCA 37 Fast Set made by Haarlem CAVEX HOLLAND B.V and which are alginate impression materials for dental use may be used to make the perineum like structure 404.

It will be appreciated by those skilled in the art that the phantom herein 400 is a combination of standard materials but it allows for focal ablation of predefined volume. The different materials used give a different MR signal that ultimately makes for a close approximation of the human prostate with a tumour inside. An MR image of the phantom herein is shown in FIG. 43.

Current practice in treating prostate cancer uses transperineal needle insertions, such as brachytherapy, PDT, photothermal, etc., through a template that fixes the needle insertion points to a grid of 5 mm spacing and orientation perpendicular to the plate. While this works reasonably well for treating the whole organ, in focal treatments, such an arrangement provides poor targeting resolution. Further, the shape and position of the planned target volume (i.e. the tumour plus some margin) may require multiple needle insertions even though the planned target volume (PTV) may be small and only require a single needle for complete coverage if restrictions on needle position and angle were relaxed. A manual oblique angle needle insertion device, with sensors to indicate needle track and position may be used for this type of surgery.

To be fully functional, a method is provided to optimize the needle trajectory and its starting position, based on complete treatment of the tumour (or PTV) and avoidance of other critical structure. The requirements of the method are therefore:

Complete treatment of the tumour Avoidance of treatment to any surrounding organs that may be at risk.

The limits of the method are therefore:

Extent of trajectory angle as determined by the device.

Extent of trajectory angle as determined by any internal bones, such as the pubic arch.

The above criteria are shown in a 2D representation at 500 in FIG. 44, and will be discussed in detail below.

Trajectory optimization requires determining the x', the starting coordinate of the needle and θ, the trajectory angle. For overlap of the treatment zone, the orientation, θ, and centre of the treatment zone ($x_c$, $y_c$) are required. The figure shows several of the requirements noted above. First, the treatment zone 502 fully covers the PTV 504. Secondly, the treatment zone 502 has minimal overlap with the organ at risk 506, but some overlap is still present. Thirdly, without the pubic arch 508, the motion of the needle is limited by the width of the device ($x_o$ to $x_{end}$). Both of these limits, and the depth of the target, restrict the trajectory angle, θ. If the pubic arch 508 is present, then the trajectory angle is further restricted. Details of resolving this are given below.

Figure 44:
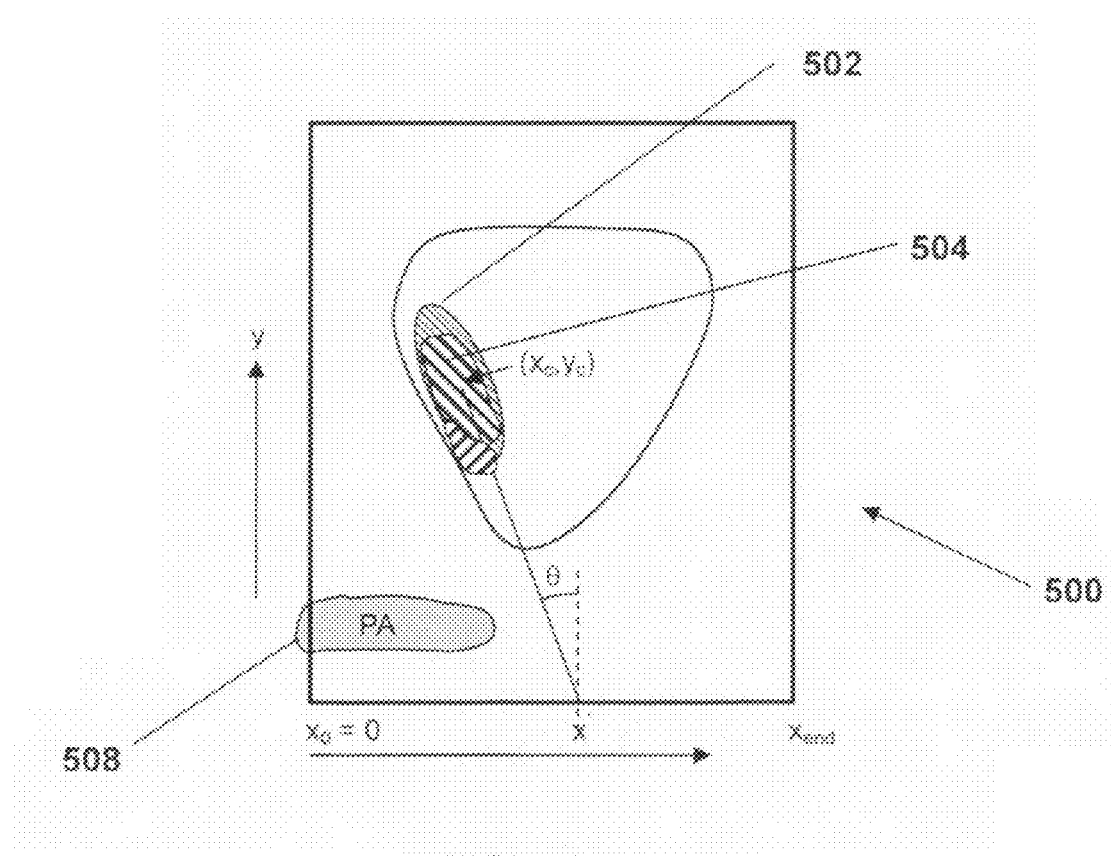
FIG. 44 is a schematic diagram of treatment parameters needed to describe optimal needle trajectory.

In FIG. 44, the treatment zone 502 for a fiber is an ellipse, with the fiber axis following along the long axis of the treatment zone. The PTV (or tumour) 504 is completely covered by the treatment zone of the light delivery fiber, which is the desired outcome. The organ at risk (OAR) 506 is also partly covered by the treatment zone, an undesirable effect. Optimization of the trajectory requires maximal overall of the treatment zone with the PTV 504, and minimal overlap with the OAR 506. To calculate the optimization, the photothermal dose delivered to the patient, $D_P$ and the resulting tissue response is considered. As a first approximation, the tissue response is considered as a simple threshold effect. In this case, treatment response, defined as $E_k$ for voxel k, can be described as:

$$E_k = \begin{Bmatrix} 0; & D_P < D_{Threshold} \\ 1; & D_P \geq D_{Threshold} \end{Bmatrix}, \qquad 1$$

where $D_{Threshold}$ is the minimum photothermal dose required to produce a coagulative response. More sophisticated models that include the full thermal dose can be used here, but our current observations indicate essentially a threshold effect. In these equations it is assumed that the threshold dose is the same for all tissue.

Figure 48:
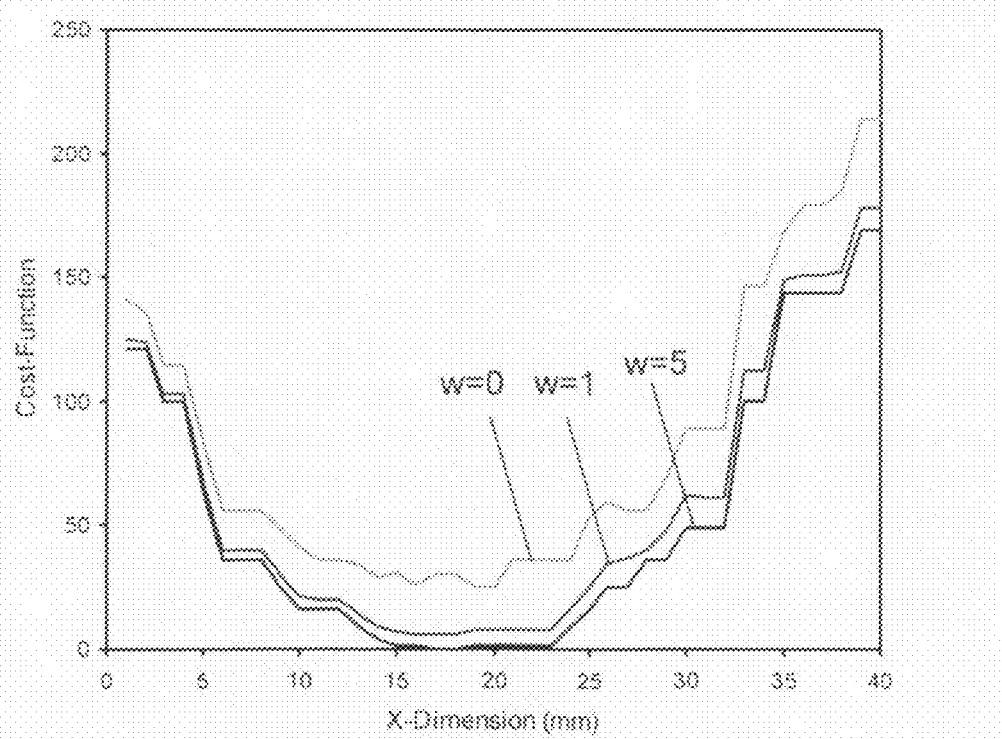
FIG. 48 is a graph showing needle position optimization for different weighting factors.

Referring to FIG. 48, to optimize the treatment delivery, the effect should be maximized for treatment of the PTV and minimized for any other tissues. In this case only a single OAR is considered. This can be summarized by the optimization/minimization of the following generalized cost function:

$$F = w_j^{PTV}\left(M - \sum_{j=1}^{M} E_j\right) + \sum_{i=1}^{N} w_j^{ORV} E_i, . \qquad 2$$

Here, the PTV and OAR have volumes of M and N voxels each. The first 2 terms describe the overlap of the PTV and the treatment effect. As more of the PTV receives a treatment above the threshold dose, the summation term increases, and the difference with the total number of voxels approaches 0. The third term represents the overlap of the OAR with the treatment zone. As more of the OAR receives a treatment above the threshold dose, this term increases in magnitude.

The effect of the dose delivered to each site, j, is weighted in the above equation using the "importance factors", $w_j$. In the instance of the OARs, the magnitude is proportional to the clinical impact of damage. If clinical outcome is not impacted, either by function or cosmetics, treatment of the OAR is "not important", and has no effect on the optimization of the treatment plan, and the dose to the OAR can be higher than the threshold dose. Conversely, if there is a clinical impact, the clinician may need to weigh the importance of possibly undertreating the PTV ($D_P<D_T$) with possibly over-treating the OAR ($D_O$>$D_T$). The relative magnitudes of the importance factors guide this balance.

Consider an example with 3 OAR's, the prostate, rectum and erectile nerves. Treatment of the normal prostate has minimal clinical effect, and so the weighting terms are set to 0 for the focal therapy. Treatment of the rectum would lead to significant clinical morbidity, and so the weighting term is set high. Treatment of the erectile nerves may depend on the patient. If it is crucial for the patient to preserve erectile function, than the weighting can be set high. If this is less important to the patient (possibly due to current conditions that limit his sexual function), then the weightings can be lower.

Optimization of the treatment requires minimizing the cost function using the centre ($x_c$, $y_c$) and orientation, $\theta$, of the treatment zone as adjustable parameters. However, these parameters will be limited by the physical limitations placed on the needle insertion, i.e. trans-perineal needle insertion using a mechanical device with size limits.

Figure 45:
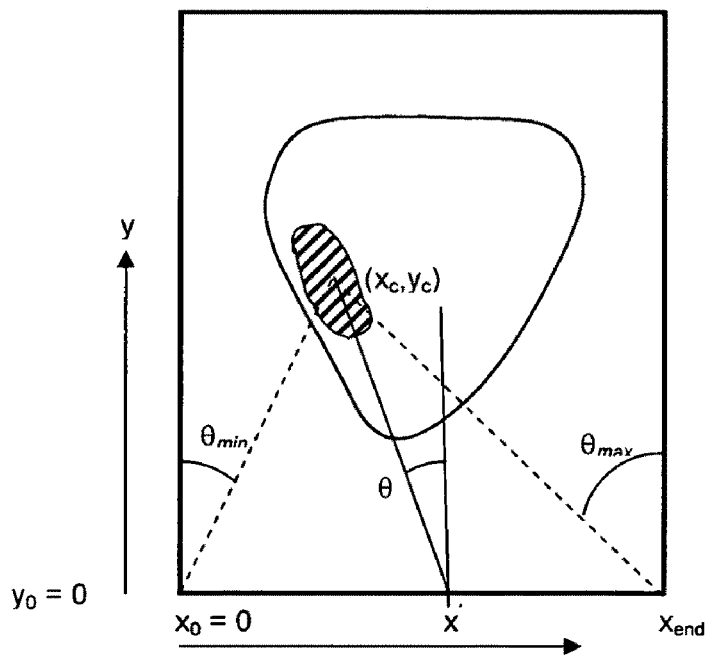
FIG. 45 is a schematic diagram of limits to needle trajectory.

The brachytherapy device has a travel limit of 10 cm, which consequently restricts the travel of the needle holder and hence the trajectory into the prostate. FIG. 45 shows the 2D limits to the needle trajectory based on the physical limits of the device. The same considerations apply in the z-coordinate. $\theta_{min}$ and $\theta_{max}$ represent the minimum and maximum angle of insertion, while $\theta$ is the optimal trajectory angle. These angles are defined not only by the travel limits of the device, but also by the position of the PTV. In this instance the centre of the PTV is taken as the target position, since this will be close to the centre of the treatment zone. Based on this, the optimal trajectory is given by:

$$\theta_{min} = \tan^{-1}((x_c - x')/y_c), \quad 3.$$

The limits to the trajectory orientation are:

$$\theta_{min} = \tan^{-1}((x_c - x_0)/y_c), \quad 3a.$$

$$\theta_{max} = \tan^{-1}((x_c - x_{end})/y_c) \quad 3b.$$

If the pubic arch interferes with the optimal trajectory, a similar approach to that given above can be used to define the limits. However, the limits need to be redefined based on the limits posed by the pubic arch.

Figure 46:
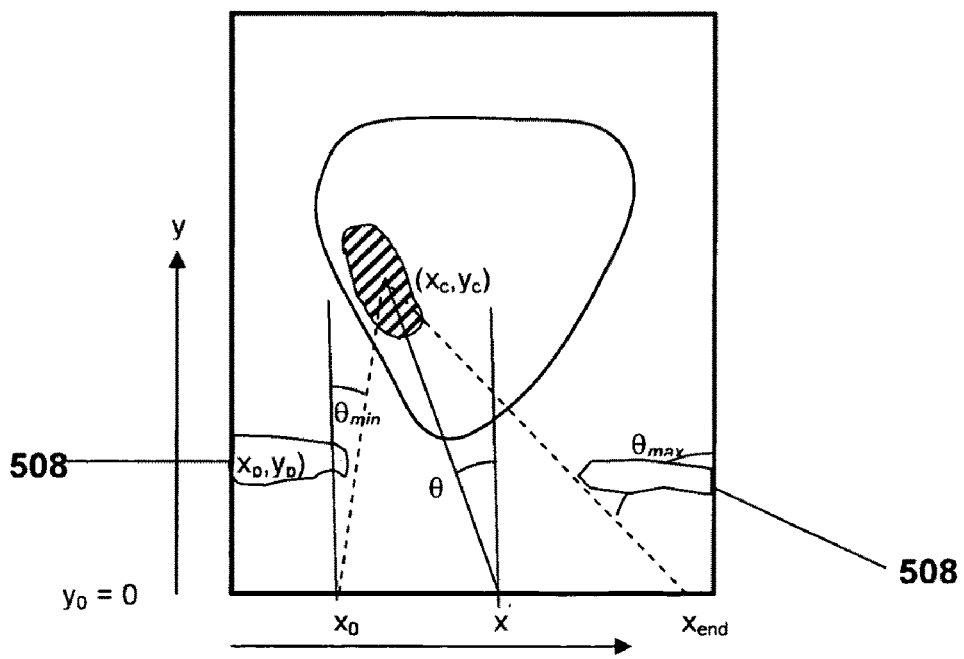
FIG. 46 is an alternate schematic diagram of limits to needle trajectory and showing two zones of interference.

The pubic arch can be considered as 2 separate left and right zones of interference as shown in FIG. 46. For each region, the appropriate extent of the pubic arch along the x-coordinate needs to be found such that the needle trajectory does not overlap with the pubic arch.

To find these limits, the centre ($x_{pc}$) and limits ($x_{pm}$, $x_{pn}$) of the each region must first be measured along the x coordinate. A line can be drawn from the PTV centre of the mass to the outer limit of the pubic arch, ($x_{pm}$, $y_{pm}$), and then further extended to needle starting position. This line will determine of the outer limits, $x_0$ and $x_{end}$. The procedure is then repeated for the other side. The following algorithm is used to find the limits:

```
xpc = mean(xp);    % centre of pubic arch along x coordinate
[xpm,imxp] = max(xp); [xpn,inxp] = min(xp); % max and min
% starting conditions matching the device limits
x_0 = 0; x_end = 40;
if xpm > xpc
    xp_t = xpm + 1;    % provides some buffer in the trajectory
    yp_t = ypm;        % matching y coordinate
    x_0 = (xp_t - xc)*yc/(yc - yp_t) + xc;   % ratio of triangles
else
    xp_t = xpn - 1;
    yp_t = ypn;
    x_end = (xp_t - xc)*yc/(yc - yp_t) + xc;
end
```

The algorithm is repeated for the other pubic region using the new limits for $x_0$ and $x_{end}$.

Initial tests of the optimization procedure were performed using MatLAB, using ($x_c$, $y_c$) and $\theta$ as adjustable parameters. The MatLAB optimization routines, however, were very insensitive to the orientation and hence were poor in finding optimal solutions. A different approach was used based on the starting needle position and the centre of the PTV. Since i) the mechanical device has a limited resolution and ii) the required resolution is approximately ±1 mm, the cost function can be calculated for the complete range of initial starting positions. The range of starting positions can be set by limits discussed above due to the pubic arch or other anatomical features. The iteration procedure then becomes.

Calculate ($x_c$, $y_c$) for PTV, based on centre of mass
For x'=$x_o$ to $x_{end}$
Calculate F for treatment zone calculated using x', ($x_c$, $y_c$)
Keeping $\theta$ fixed, minimize F by varying ($x_c$, $y_c$)
If $F_k$<$F_{k-1}$ return, else store ($x_c$, $y_c$) and continue
Find x' with minimal F, and calculate trajectory based on x', and ($x_c$, $y_c$)
Another approach would use standard optimization routines and minimize the cost function by simultaneously adjusting ($x_c$, $y_c$) and $\theta$, with limits determined by the pubic arch.

Figure 47:
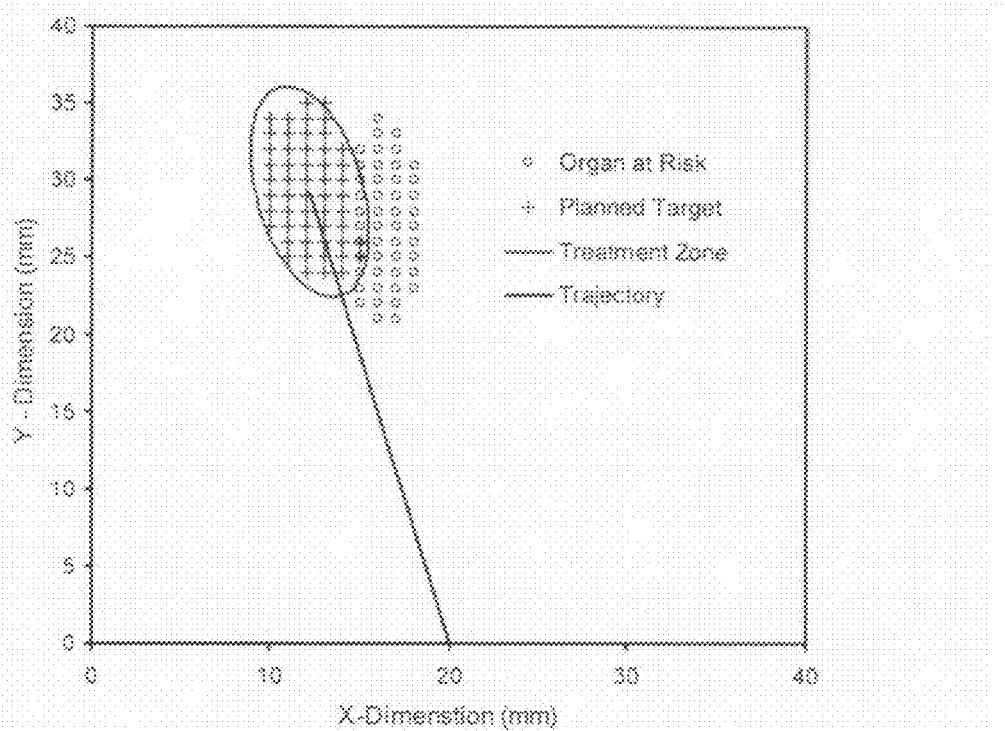
FIG. 47 is a schematic showing the optimal needle trajectory and position of the treatment zone.

A 2D example of the needle trajectory optimization is shown in FIG. 47. Here the planned target volume is not perpendicular to the needle template plane (defined by the x-axis). An organ at risk lies adjacent to the PTV. The figure on the right shows the cost-function value using different weighting values for the OAR ($w_{OAR}$ in Eqn. 2). When $w^{OAR}$=0, as with the blue line in the FIG. 4b, the cost function only reaches 0 when the target zone completely overlaps the PTV. This only occurs when the starting needle position is at 16-17 mm, with the needle aimed at the centre of the PTV. Adding some weighting to the OAR increases the cost function, and slightly changes the optimal needle trajectory. However, in this case the cost function never completely goes to 0 since some of the OAR falls within the Treatment Zone.

The above example demonstrates the process in 2 dimensions. Extension to 3 dimensions requires optimization of not just x' and $\theta$, but instead (x', y') and ($\theta$, $\phi$)

A needle tracking optimization method has been developed that includes maximizing total dose to the planned target volume while minimizing the dose to any surrounding critical organs and to avoid any objects that are potentially in the path of the needle. The current model uses a simple method of accounting for the treatment response. More sophisticated models that incorporate the thermal dose can also be applied. Further, avoidance of the critical structures can also incorporate dose models that account for clinical morbidity due to the creation of hot spots within the organ. For instance, in avoiding the rectum, the plan may lead to little dose in the organ as a whole, but if the entire dose is at a single hot spot, then it can lead to an adverse event.

It will be appreciated by those skilled in the art that the above discussion may be generalized as a method to determine the needle trajectory comprising the steps of: providing images of a predetermined area; determining the location of an irregular zone on the images; calculating a planned target volume from the location of the irregular zone; calculating the treatment zone whereby the treatment zone covers the planned target volume; determining the starting needle position within a predetermined range; and calculating the needle trajectory from the starting needle position to the planned target zone. This can be enhanced by including the steps of determining the location of at least one zone at risk on the images; and determining the location of at least one avoidance zone from images and wherein calculating the needle trajectory includes factors to avoid the avoidance zones. In most instances the zone at risk is an organ, the irregular zone is a tumor and each avoidance zone is a bone. Preferably the images are magnetic resonance images. Further, the method may include the steps of determining from the images a temperature evaluation image and determining from the temperature evaluation image if an actual treatment zone equals the planned treatment zone.

Generally speaking, the systems described herein are directed to medical robots and medical instrument assemblies. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to medical robots and medical instrument assemblies.

As used herein, the terms "comprises" and "comprising" are to be construed as being inclusive and opened rather than exclusive. Specifically, when used in this specification including the claims, the terms "comprises" and "comprising" and variations thereof mean that the specified features, steps or components are included. The terms are not to be interpreted to exclude the presence of other features, steps or components.

What is claimed as the invention is:

1. A medical robot for use inside a magnetic resonance imager having an axial plane defined by a vertical axis and a sagittal plane defined by the lateral axis, the medical robot being connectable to a medical instrument assembly comprising:
   a horizontal motion assembly including a horizontal motion joint, a horizontal ultrasonic motor operably connected to said horizontal motion joint and a horizontal encoder operably connected to said horizontal ultrasonic motor, wherein said horizontal ultrasonic motor and said horizontal encoder are positioned proximate to said horizontal motion joint;
   a vertical motion assembly operably connected to the horizontal motion assembly, the vertical motion assembly including a vertical motion joint, a vertical ultrasonic motor operably connected to said vertical motion joint and a vertical encoder operably connected to said vertical ultrasonic motor, wherein said vertical ultrasonic motor and said vertical encoder are positioned proximate to said vertical motion joint and the medical instrument assembly is operably connectable to one of said vertical motion joint and said horizontal motion joint; and
   a controller operably connected to the horizontal motion joint and the vertical motion joint;
   wherein the ultrasonic motors each has a corresponding cross section positioned in a plane selected from the group consisting of the sagittal plane and axial plane of the magnetic resonance imager.

2. The medical robot as claimed in claim 1 further including a pan assembly operably connected to one of the vertical motion assembly and the horizontal motion assembly and the medical instrument assembly is operably connectable to one of the pan assembly, the vertical motion assembly and the horizontal motion assembly, the pan assembly including a pan joint, a pan ultrasonic motor operably connected to the pan joint and a pan encoder operably connected to the pan ultrasonic motor, the pan ultrasonic motor and pan encoder are positioned proximate to the pan joint, the pan ultrasonic motor is positioned in one of the axial and sagittal plane and the pan assembly is operably connected to the controller.

3. The medical robot as claimed in claim 2 further including a tilt assembly operably connected to one of the pan assembly, the vertical motion assembly and the horizontal motion assembly and the medical instrument assembly is operably connectable to one of the tilt assembly, the pan assembly, the vertical motion assembly and the horizontal motion assembly, the tilt assembly including a tilt joint, a tilt ultrasonic motor operably connected to the tilt joint and a tilt encoder operably connected to the tilt ultrasonic motor, the tilt ultrasonic motor and the tilt ultrasonic motor are positioned proximate to the tilt joint, said tilt ultrasonic motor is positioned in one of the axial and sagittal plane and the tilt assembly is operably connected to the controller.

4. The medical robot as claimed in claim 3 further including a roll assembly operably connected to one of the tilt assembly, the pan assembly, the vertical motion assembly and the horizontal motion assembly and the medical instrument assembly is operably connectable to one of the roll assembly, the tilt assembly, the pan assembly, the vertical motion assembly and the horizontal motion assembly, the roll assembly including a roll joint and a roll ultrasonic motor operably connected to the roll joint and a roll encoder operably connected to the roll ultrasonic motor, the roll ultrasonic motor and the roll encoder are positioned proximate to the roll joint, said roll ultrasonic motor is positioned in one of the axial and sagittal plane, and the roll assembly is operably connected to the controller.

5. The medical robot as claimed in claim 4 wherein the tilt assembly and the roll assembly are a combined tilt and roll assembly.

6. The medical robot as claimed in claim 5 wherein the horizontal motion assembly further includes a horizontal lead screw operably connected to the ultrasonic motor of the horizontal motion assembly, a pair of spur gears operably connected between said horizontal lead screw and a horizontal plate.

7. The medical robot as claimed in claim 6 wherein the vertical motion assembly further includes a vertical lead screw operably connected to the ultrasonic motor of the vertical motion assembly and a timing belt and pair of pulleys operably connected between said vertical lead screw and a vertical plate.

8. The medical robot as claimed in claim 7 wherein the pan motion assembly further includes a pan shaft assembly operably connected to the pan ultrasonic motor, a timing belt and pulleys operably connected to the pan shaft assembly and operably connectable to the medical instrument assembly.

9. The medical robot as claimed in claim 8 wherein the combined tilt and roll assembly further includes a bevel gear differential mechanism operably connected to the tilt ultrasonic motor and the roll ultrasonic motor and the bevel gear differential mechanism is operably connectable to the medical instrument assembly.

10. The medical robot as claimed in claim 9 wherein each of the ultrasonic motors is positioned a predetermined distance from a local coil used in the magnetic resonance imager whereby the positioning thereof reduces electromagnetic interaction with the magnetic resonance imager.

11. The medical robot as claimed in claim 10 further including gears operably connected to at least one of the ultrasonic motors.

12. The medical robot as claimed in claim 11 further including a gears attached to each of the ultrasonic motors.

13. The medical robot as claimed in claim 4 wherein the medical instrument assembly is a trocar and the trocar is operably connected to the controller.

14. The medical robot as claimed in claim 4 wherein the medical instrument assembly includes a pushing and pulling mechanism operably connected to an ultrasonic motor positioned proximate thereto.

15. The medical robot as claimed in claim 14 wherein the pushing and pulling mechanism includes a pushing and pulling lead screw operably connected to the ultrasonic motor, a holder operably connected to the pushing and pulling lead screw and the holder being adapted to hold a laser applicator and further including a locker operably connected to the lead screw.

16. The medical robot as claimed in claim 15 wherein the medical instrument assembly further includes a pneumatically driven tapping block operably connected to the pushing and pulling mechanism.

17. The medical robot as claimed in claim 16 wherein a combination of the medical robot and the medical instrument assembly is a six degree of freedom medical robot and the ultrasonic motors are adapted to be positionable within the isocentre of the medical resonance imager.

18. The medical robot as claimed in claim 15 whereby the controller is rapidly turned on and off interleaved between the turning on the magnetic imager, imaging and turning off of the magnetic resonance imager, thereby interleaving the imaging with movement.

19. The medical robot as claimed in claim 18 whereby the imaging includes imaging sequences whereby the imaging sequences are one of a gradient echo pulse sequence with a short echo time and a fast-spin-echo pulse sequence with a short echo time.

20. The medical robot as claimed in claim 18 whereby the imaging includes imaging sequences whereby the imaging sequences include three different pulse sequences including long-TE FSE, T1-weighted FSE, and short-TR gradient echo.

21. The medical robot as claimed in claim 14 wherein the medical instrument assembly further includes one of a laser diffuser with a retractable titanium sheath, a biopsy tool and a brachytherapy tool.

22. The medical robot as claimed in claim 4 further including a control system operably connected to the controller and remote from and isolated from the controller.

23. The medical robot as claimed in claim 22 wherein the control system is isolated by one of a predetermined distance and magnetically isolated.

24. The medical robot as claimed in claim 4 further including a calibration phantom attached to the medical instrument assembly.

25. The medical robot as claimed in claim 24 wherein the calibration phantom includes a housing that is attachable to a predetermined location on the medical instrument, at least one channel formed in the housing capable of being visible in a magnetic resonance image, the channel being at a predetermined location to a point of interest in the medical instrument.

26. The medical robot as claimed in claim 25 wherein the at least one channel is a plurality of channels.

27. The medical robot as claimed in claim 26 wherein there are four channels.

28. The medical robot as claimed in claim 25 wherein the at least one channel is an annular ring.

29. The medical robot as claimed in claim 25 wherein each channel is filled with a mixture of water and magnetic resonance imager visible fluid.

30. The medical robot as claimed in claim 4 wherein the medical instrument includes a laser fiber having a surrounding channel filled with a mixture of water and magnetic resonance imager visible fluid.

31. The medical robot as claimed in claim 4 further including a platform having a robot guide adapted to receive the medical robot and a patient receiving portion adapted to adjustably position a patient thereon.

32. The medical robot as claimed in claim 31 wherein the platform includes a base and the patient receiving portion includes a haunch support hingeably attached to the base and a leg support hingeably attached to the haunch support.

33. The medical robot as claimed in claim 32 wherein the patient receiving portion further includes an adjustable mechanism assembly operably connected to the leg support whereby movement of the adjustable mechanism repositions the haunch support relative to the leg support.

34. The medical robot as claimed in claim 33 further including a pair of guides one on each side of the base and the adjustable mechanism assembly engages the guides and is moveable along the guides.

35. The medical robot as claimed in claim 34 wherein the robot is moveable along the guides.

* * * * *